(12) United States Patent
Iemoto

(10) Patent No.: US 12,409,106 B2
(45) Date of Patent: Sep. 9, 2025

(54) MEDICAL MATERIAL

(71) Applicant: Senju USA, Inc., Torrance, CA (US)

(72) Inventor: Suzuka Iemoto, Osaka (JP)

(73) Assignee: Senju USA, Inc., Torrance, CA (US)

(*) Notice: Subject to any disclaimer, the term of this patent is extended or adjusted under 35 U.S.C. 154(b) by 0 days.

(21) Appl. No.: 18/922,818

(22) Filed: Oct. 22, 2024

(65) Prior Publication Data

US 2025/0041164 A1 Feb. 6, 2025

Related U.S. Application Data

(63) Continuation of application No. 18/894,551, filed on Sep. 24, 2024, which is a continuation-in-part of application No. PCT/JP2023/013420, filed on Mar. 30, 2023.

(30) Foreign Application Priority Data

Mar. 31, 2022 (JP) .................................. 2022-060562

(51) Int. Cl.
A61K 6/69 (2020.01)
A61K 6/20 (2020.01)
A61K 6/80 (2020.01)
A61K 6/84 (2020.01)

(52) U.S. Cl.
CPC .................. A61K 6/69 (2020.01); A61K 6/20 (2020.01); A61K 6/80 (2020.01); A61K 6/84 (2020.01)

(58) Field of Classification Search
None
See application file for complete search history.

(56) References Cited

U.S. PATENT DOCUMENTS

| 4,291,013 | A | * | 9/1981 | Wahlig .................. A61L 15/325 424/572 |
| 4,789,662 | A | | 12/1988 | Thomas-Leurquin et al. |
| 4,906,670 | A | | 3/1990 | Higashi et al. |
| 5,447,940 | A | * | 9/1995 | Harvey .................. A61L 31/129 424/443 |
| 5,660,857 | A | | 8/1997 | Haynes et al. |
| 5,789,465 | A | | 8/1998 | Harvey et al. |

(Continued)

FOREIGN PATENT DOCUMENTS

| JP | 62-223115 | 10/1987 |
| JP | 62-228029 | 10/1987 |

(Continued)

OTHER PUBLICATIONS

Stephen M. Berge, Lyle D. Bighley, and Donald C. Monkhouse. "Pharmaceutical Salts." Journal of Pharmaceutical Sciences, vol. 66 No. 1, Jan. 1977, pp. 1-19. (Year: 1977).*

(Continued)

Primary Examiner — Isaac Shomer
(74) Attorney, Agent, or Firm — Wenderoth, Lind & Ponack, L.L.P.

(57) ABSTRACT

It is an object of the present disclosure to provide a novel dental preparation for use in the treatment of a tissue defect. The dental preparation contains a shaped body obtained by drying a raw material aqueous solution containing collagen and/or gelatin (A), a free form and/or alkali metal salt of bromfenac (B), and a water-soluble divalent metal salt (C).

9 Claims, 6 Drawing Sheets

(56) References Cited

U.S. PATENT DOCUMENTS

| | | | |
|---|---|---|---|
| 6,001,895 A | 12/1999 | Harvey et al. | |
| 6,015,844 A * | 1/2000 | Harvey | A61L 27/48 |
| | | | 523/105 |
| 2013/0316006 A1 * | 11/2013 | Popov | A61P 5/44 |
| | | | 424/490 |
| 2014/0039056 A1 * | 2/2014 | Liu | A61K 31/13 |
| | | | 514/567 |
| 2015/0125539 A1 * | 5/2015 | Popov | A61K 9/5031 |
| | | | 424/497 |

FOREIGN PATENT DOCUMENTS

| | | |
|---|---|---|
| JP | 3-23864 | 1/1991 |
| JP | 7-116241 | 5/1995 |
| JP | 7-179361 | 7/1995 |

OTHER PUBLICATIONS

Tatsuro Ishii, Hitoshi Nishimura, Masamichi Komiya, Yoshiaki Akirnoto and Takeo Nakamura. "Clinical Evaluation of Bullet-Shaped Atelocollagen Sponge (Teruplug®) as Protective Material for Tooth Extraction Wounds." Dental Outlook, vol. 97, No. 2, 2001, pp. 1-23 (English) and 24-36(Japanese). (Year: 2001).*
International Search Report issued Jun. 13, 2023 in International (PCT) Application No. PCT/JP2023/013420.

* cited by examiner

MEDICAL MATERIAL

CROSS-REFERENCE TO RELATED APPLICATIONS

This application is a continuation of U.S. application Ser. No. 18/894,551, filed Sep. 24, 2024, which is a continuation-in-part of International Application No. PCT/JP2023/013420, filed Mar. 30, 2023, which claims priority to Japanese Patent Application No. 2022-060562, filed Mar. 31, 2022, each of which is incorporated by reference herein in its entirety.

TECHNICAL FIELD

The present disclosure relates to a dental preparation used for the treatment of a tissue defect, such as an extraction socket.

BACKGROUND ART

Conventionally, in the treatment of a tissue defect, such as an extraction socket, the tissue defect is filled with a block-shaped filling and/or coated with a sheet-shaped coating material for the purpose of hemostasis, promotion of tissue regeneration, prevention of contracture, and prevention of infection, and the like. Such a filling and coating material need to be absorbed by a living body together with tissue regeneration to replace a tissue while also functioning as a scaffold for tissue regeneration, and therefore a biocompatible material having biocompatibility and bioabsorbability is used.

Conventionally, various fillings and coating materials using biocompatible materials have been reported. For example, Patent Document 1 describes that a filling for biological tissue including a composite material of a collagen sponge and a biodegradable absorbent polymer material has a small tissue reaction, promotes the proliferation of fibroblasts, and maintains its shape and strength for a long period of time. Patent Document 2 describes that an absorbent biomaterial composed of thermally crosslinked chitin or a derivative thereof is excellent in affinity with a living body, exhibits an appropriate decomposition absorption rate in the living body, and can be used as a filling or a coating material.

PRIOR ART DOCUMENTS

Patent Documents

Patent Document 1: JP 1991-23864 A
Patent Document 2: JP 1995-116241 A

SUMMARY OF THE INVENTION

Means for Solving the Problem

A shaped body is obtained by drying an aqueous solution to which collagen and/or gelatin (A), a free form and/or alkali metal salt of bromfenac (B), and a water-soluble divalent metal salt (C) are added. The present inventor has found that the shaped body, has a high release rate of bromfenac until at least 3 hours after application to a tissue defect such as an extraction socket, can continuously release bromfenac for at least 7 days after application, and can have a suitable drug release profile.

The present inventor has also found that when, in the shaped body, a divalent metal salt of bromfenac and a free form and/or alkali metal salt of bromfenac coexist in a matrix formed of the collagen and/or gelatin, the free form and/or alkali metal salt of bromfenac is mainly released until at least 3 hours after application to the tissue defect such as an extraction socket, and bromfenac constituting the divalent metal salt of bromfenac is slowly released over at least 7 days, thereby enabling the drug release profile. Furthermore, it has also been found that the shaped body can improve the stability of bromfenac due to long-term storage or heat exposure. The present disclosure has been completed by further conducting studies based on such findings.

In an embodiment of the present disclosure, there are provided a dental preparation and a method for producing the same according to the following aspects.

Item 1-1. A dental preparation containing a shaped body obtained by drying a raw material aqueous solution containing collagen and/or gelatin (A), a free form and/or alkali metal salt of bromfenac (B), and a water-soluble divalent metal salt (C).

Item 1-2. The dental preparation according to item 1-1, wherein the free form and/or alkali metal salt of bromfenac (B) is bromfenac sodium.

Item 1-3. The dental preparation according to item 1-1 or 1-2, wherein the water-soluble divalent metal salt (C) is at least one selected from the group consisting of a water-soluble calcium salt, a water-soluble magnesium salt, and a water-soluble zinc salt.

Item 1-4. The dental preparation according to any one of items 1-1 to 1-3, wherein the water-soluble divalent metal salt (C) is at least one selected from the group consisting of calcium chloride, magnesium chloride, and zinc sulfate.

Item 1-5. The dental preparation according to any one of items 1-1 to 1-4, wherein the collagen and/or gelatin (A) is atelocollagen.

Item 1-6. The dental preparation according to item 1-5, wherein a type of the atelocollagen is type I or type III.

Item 1-7. The dental preparation according to any one of items 1-1 to 1-6, wherein the collagen and/or gelatin (A) is porcine-derived atelocollagen or bovine-derived atelocollagen.

Item 1-8. The dental preparation according to any one of items 1-1 to 1-7, wherein the amount of the collagen and/or gelatin (A) added in the raw material aqueous solution is about 0.01 to 3 w/v %.

Item 1-9. The dental preparation according to any one of items 1-1 to 1-8, wherein the amount of the free form and/or alkali metal salt of bromfenac (B) added in the raw material aqueous solution is about 0.01 to 5 w/v %.

Item 1-10. The dental preparation according to any one of items 1-1 to 1-9, wherein in the raw material aqueous solution, the water-soluble divalent metal salt (C) is added so as to satisfy a ratio of about 0.01 to 5 Eq as an equivalent in terms of divalent metal atom per 1 Eq as an equivalent in terms of free form of the free form and/or alkali metal salt of bromfenac (B).

Item 1-11. The dental preparation according to any one of items 1-1 to 1-10, wherein the content of the collagen and/or gelatin (A) per 1 g of the shaped body is about 10 to 990 mg.

Item 1-12. The dental preparation according to any one of items 1-1 to 1-11, wherein the content of bromfenac per 1 g of the shaped body is about 1 to 800 mg as an amount of bromfenac in terms of free form.

Item 1-13. The dental preparation according to any one of items 1-1 to 1-12, wherein the shaped body is a porous body.

Item 1-14. The dental preparation according to any one of items 1-1 to 1-13, wherein the shaped body has a bullet shape.

Item 1-15. The dental preparation according to any one of items 1-1 to 1-14, wherein the dental preparation is used as a filling or a coating material for a tissue defect in a dental region.

Item 1-16. The dental preparation according to item 1-15, wherein the tissue defect is an extraction socket.

Item 1-17. A method for producing a dental preparation, the method including the step of drying a raw material aqueous solution containing collagen and/or gelatin (A), a free form and/or alkali metal salt of bromfenac (B), and a water-soluble divalent metal salt (C) to obtain a shaped body.

In another embodiment of the present disclosure, there is provided a dental preparation of the following aspects.

Item 2-1. A dental preparation containing a free form and/or alkali metal salt of bromfenac, and a divalent metal salt of bromfenac in a matrix formed of collagen and/or gelatin.

Item 2-2. The dental preparation according to item 2-1, wherein the free form and/or alkali metal salt of bromfenac is bromfenac sodium.

Item 2-3. The dental preparation according to item 2-1 or 2-2, wherein the divalent metal salt of bromfenac is at least one selected from the group consisting of a calcium salt of bromfenac, a magnesium salt of bromfenac, and a zinc salt of bromfenac.

Item 2-4. The dental preparation according to any one of items 2-1 to 2-3, wherein the collagen and/or gelatin is atelocollagen.

Item 2-5. The dental preparation according to item 2-4, wherein a type of the atelocollagen is type I or type III.

Item 2-6. The dental preparation according to any one of items 2-1 to 2-5, wherein the collagen and/or gelatin is porcine-derived atelocollagen or bovine-derived atelocollagen.

Item 2-7. The dental preparation according to any one of items 2-1 to 2-6, wherein the content of the collagen and/or gelatin per 1 g of the dental preparation is about 10 to 990 mg.

Item 2-8. The dental preparation according to any one of items 2-1 to 2-7, wherein the content of bromfenac per 1 g of the dental preparation is about 1 to 800 mg as an amount of bromfenac in terms of free form.

Item 2-9. The dental preparation according to any one of items 2-1 to 2-8, wherein the dental preparation is a porous body.

Item 2-10. The dental preparation according to any one of items 2-1 to 2-9, wherein the dental preparation has a bullet shape.

Item 2-11. The dental preparation according to any one of items 2-1 to 2-10, wherein the dental preparation is used as a filling or a coating material for a tissue defect in a dental region.

Item 2-12. The dental preparation according to item 2-11, wherein the tissue defect is an extraction socket.

In still another embodiment of the present disclosure, there is provided a treatment method of the following aspects.

Item 3-1. A method for treating a tissue defect, the method including the step of filling or coating a tissue defect in a dental region with a dental preparation containing a shaped body obtained by drying a raw material aqueous solution containing collagen and/or gelatin (A), a free form and/or alkali metal salt of bromfenac (B), and a water-soluble divalent metal salt (C).

Item 3-2. The method according to item 3-1, wherein the tissue defect is an extraction socket.

Item 3-3. The method according to item 3-1 or 3-2, wherein the dental preparation releases an effective amount of bromfenac and maintains its shape over at least 7 days.

Item 3-4. The method according to any one of items 3-1 to 3-3, wherein pain involving the tissue defect is alleviated by an anti-inflammatory analgesic effect and a wound protective effect.

In yet still another embodiment of the present disclosure, there is provided a treatment method of the following aspects.

Item 4-1. A method for treating a tissue defect, the method including the step of filling or coating a tissue defect in a dental region with a dental preparation containing a free form and/or alkali metal salt of bromfenac, and a divalent metal salt of bromfenac in a matrix formed of collagen and/or gelatin.

Item 4-2. The method according to item 4-1, wherein the tissue defect is an extraction socket.

Item 4-3. The method according to item 4-1 or 4-2, wherein the dental preparation releases an effective amount of bromfenac and maintains its shape over at least 7 days.

Item 4-4. The method according to any one of items 4-1 to 4-3, wherein pain involving the tissue defect is alleviated by an anti-inflammatory analgesic effect and a wound protective effect.

In further another embodiment of the present disclosure, there is provided a treatment method of the following aspects.

Item 5-1. A method for treating pain involving a tissue defect, the method including the step of filling or coating a tissue defect in a dental region with a dental preparation containing a shaped body obtained by drying a raw material aqueous solution containing collagen and/or gelatin (A), a free form and/or alkali metal salt of bromfenac (B), and a water-soluble divalent metal salt (C).

Item 5-2. The method according to item 5-1, wherein the tissue defect is an extraction socket.

Item 5-3. The method according to item 5-1 or 5-2, wherein the dental preparation releases an effective amount of bromfenac and maintains its shape over at least 7 days.

Item 5-4. The method according to any one of items 5-1 to 5-3, wherein the treatment method has an anti-inflammatory analgesic effect and a wound protective effect.

In further another embodiment of the present disclosure, there is provided a treatment method of the following aspects.

Item 6-1. A method for treating pain involving a tissue defect, the method including the step of filling or coating a tissue defect in a dental region with a dental preparation containing a free form and/or alkali metal salt of bromfenac, and a divalent metal salt of bromfenac in a matrix formed of collagen and/or gelatin.

Item 6-2. The method according to item 6-1, wherein the tissue defect is an extraction socket.

Item 6-3. The method according to item 6-1 or 6-2, wherein the dental preparation releases an effective amount of bromfenac and maintains its shape over at least 7 days.

Item 6-4. The method according to any one of items 6-1 to 6-3, wherein the method has an anti-inflammatory analgesic effect and a wound protective effect.

Advantageous of the Invention

According to an embodiment of a dental preparation of the present disclosure, there is provided a dental preparation having a high release rate of bromfenac until at least 3 hours after application to a tissue defect (such as an extraction socket) in a dental region, and capable of continuously releasing bromfenac for at least 7 days after application. In a suitable embodiment of the dental preparation of the present disclosure, bromfenac can be rapidly released at a release rate of 3.6 μg/hour or more until at least 3 hours after application to a tissue defect in a dental region, and bromfenac can be continuously released at a release rate of 0.36 μg/hour or more for at least 7 days after application. Therefore strong pain felt when anesthesia is worn off after surgery and intolerable pain that lasts for about 7 days thereafter can be effectively alleviated.

According to an embodiment of the dental preparation of the present disclosure, the shape can be stably maintained even 7 days after application to a tissue defect in a dental region, and therefore the dental preparation can sufficiently function as a scaffold for tissue regeneration. Since the dental preparation of the present disclosure has biocompatibility and bioabsorbability, the dental preparation is absorbed in a living body and disappears after functioning as a scaffold for tissue regeneration. Therefore it is not necessary to remove the dental preparation after surgery, and the burden on a patient can be reduced.

According to an embodiment of the dental preparation of the present disclosure, the decomposition of bromfenac due to long-term storage or heat exposure can also be suppressed, and therefore excellent storage stability can be provided.

EMBODIMENTS OF THE INVENTION

1. Definitions

Figure 1:
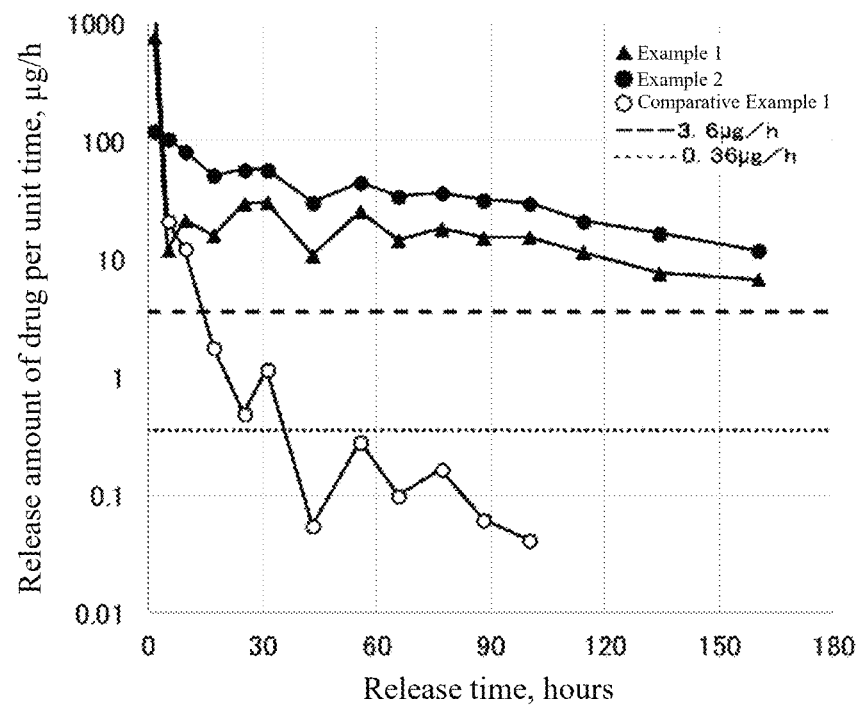
FIG. 1 is a view showing a temporal change in the release amount of bromfenac per unit time for a collagen sponge preparation of each of Examples 1 and 2 and Comparative Example 1.

It should be understood that terms used in the present disclosure are used in meanings commonly used in the art unless otherwise stated. Thus, unless defined otherwise, all technical terms and scientific terms used herein have the same meanings as those commonly understood by one of ordinary skill in the art to which the present disclosure pertains. In case of conflict, the present disclosure (including definitions) will take precedence.

In the present disclosure, a "dental preparation" refers to a preparation used in a dental field.

In the present disclosure, a "shaped body" refers to a solid material having a three-dimensional structure of a predetermined shape.

In the present disclosure, a "matrix formed of collagen and/or gelatin" refers to a three-dimensional structure composed of at least one of collagen and gelatin.

In the present disclosure, a "free form of bromfenac" refers to bromfenac (bromfenac free acid) in the form of a salt. In the present disclosure, the term "bromfenac" includes all of a free form of bromfenac, an alkali metal salt thereof, and a divalent metal salt thereof.

In the present disclosure, an "amount of bromfenac in terms of free form" refers to the amount of bromfenac itself in case of free form. In case of an alkali metal salt of bromfenac, an "amount of bromfenac in terms of free form" refers to a value obtained by converting the amount of the alkali metal salt of bromfenac as the amount of the free form of bromfenac. In case of a divalent metal salt of bromfenac, an "amount of bromfenac in terms of free form" refers to a value obtained by converting the divalent metal salt of bromfenac as the amount of the free form of bromfenac.

In the present disclosure, an "equivalent" is a value (Eq, equivalent) obtained by multiplying the number of moles of a component by an ionic valence.

In the present disclosure, regarding the free form of bromfenac, the alkali metal salt thereof, and the divalent metal salt thereof, an "equivalent in terms of free form" is a value obtained by converting the free form of bromfenac, the alkali metal salt thereof, and the divalent metal salt thereof as the equivalent of the free form of bromfenac. Since the ionic valence of the free form of bromfenac is 1, 1 mol of the free form of bromfenac, 1 mol of the alkali metal salt of bromfenac, and 1 mol of the divalent metal salt of bromfenac each have an equivalent of 1 Eq in terms of free form.

Regarding a water-soluble divalent metal salt, an "equivalent in terms of divalent metal atom" is a value obtained by converting the water-soluble divalent metal salt as an equivalent of divalent metal atom. Since the ionic valence of the divalent metal atom is 2, the equivalent of 1 mol of the water-soluble divalent metal salt in terms of divalent metal atom is 2 Eq.

In the present disclosure, an "effective amount of bromfenac is released" means that an amount of bromfenac effective for pain alleviation is released. As an example of an aspect in which an effective amount of bromfenac is released, bromfenac is rapidly released at a release rate of 3.6 µg/hour or more until at least 3 hours after application to a tissue defect, and bromfenac is continuously released at a release rate of 0.36 µg/hour or more for at least 7 days after application.

In the present disclosure, "maintain a shape" means that the shape is held to such an extent that a function as a filling or a coating material can be maintained. For example, in evaluation due to appearance observation and an image area after immersion in PBS (−), i.e., phosphate buffered saline without $Ca^{2+}$ and $Mg^{2+}$, and shaking at 37° C. for 168 hours, when the degree of disintegration of the preparation is smaller than that of the same preparation except that the water-soluble divalent metal salt is not used, the shape is determined to be maintained.

2. Description of Preferred Embodiments

Although descriptions of preferred embodiments are set forth below, it should be understood that the embodiments are illustrative of the present disclosure and the scope of the disclosure is not limited to such preferred embodiments. It should be understood that those skilled in the art can also easily make modifications and changes and the like within the scope of the present disclosure with reference to the following preferred Examples. For these embodiments, those skilled in the art may appropriately combine any embodiments.

3. Dental Preparation (1)

Conventionally, a dental preparation used as a filling for a tissue defect has a desired shape, and has a matrix formed of a biocompatible polymer, and therefore the dental preparation is biocompatible, but cannot suppress pain and inflammation. Meanwhile, since bromfenac has an anti-inflammatory analgesic effect, the dental preparation is expected to have the anti-inflammatory analgesic effect by adding a nonsteroidal anti-inflammatory drug to the dental preparation. Usually, anesthesia is worn off 2 to 3 hours after surgery to cause strong pain, and then the strong pain subsides. Therefore, when the dental preparation containing the nonsteroidal anti-inflammatory drug is used as a filling or a coating material for a tissue defect, it is desirable that the drug elution profile of the dental preparation has a high release rate of the nonsteroidal anti-inflammatory drug until at least 3 hours after surgery, and continuously releases the nonsteroidal anti-inflammatory drug until at least day 7 after surgery.

Meanwhile, bromfenac is a kind of phenylacetic acid-based nonsteroidal anti-inflammatory drug, and is effective in alleviating pain after oral surgery. Conventionally, bromfenac has been widely used in the form of a sodium salt (bromfenac sodium), but the present inventor has found that when a shaped body in which bromfenac sodium is supported in a matrix formed of a biocompatible polymer under specific conditions is applied to a tissue defect, there are problems that bromfenac is rapidly released to shorten the duration of an anti-inflammatory analgesic effect, and a risk of safety is caused by release of an excessive amount of bromfenac at a time, and the above-described drug elution profile cannot be achieved.

Therefore, an object of one embodiment of the present disclosure is to provide a preparation technology that achieves a drug elution profile having a high release rate of bromfenac until at least 3 hours after application to the tissue defect such as an extraction socket, and capable of continuously releasing bromfenac for at least 7 days after application when a dental preparation containing bromfenac is used for the treatment of a tissue defect such as an extraction socket.

The present inventor has extensively conducted studies for achieving the above-mentioned object, and resultantly found that a shaped body obtained by drying a raw material aqueous solution to which collagen and/or gelatin (A), a free form and/or alkali metal salt of bromfenac (B), and a water-soluble divalent metal salt (C) are added has a high release rate of bromfenac until at least 3 hours after application to a tissue defect such as an extraction socket, can continuously release bromfenac for at least 7 days after application, and can have a suitable drug release profile as a dental preparation to be used for the treatment of the tissue defect.

When the dental preparation containing bromfenac is used as a filling or a coating material for a tissue defect, it is particularly suitable that the concentration of bromfenac in the tissue defect is 10 times or more of a 50% effective concentration ($EC_{50}$) until at least 3 hours after surgery to alleviate strong pain when anesthesia is worn off, and the concentration of bromfenac in the tissue defect is maintained at $EC_{50}$ or more for at least 7 days after surgery. The topical 50% effective concentration of bromfenac $EC_{50}$ on pain after oral surgery is reported to be 0.36 µg/mL (Soong T. Chiang et al., Pharmacotherapy, Vol. 16, No. 6, 1996, p. 1179-1187). It is considered that the retention time of a body fluid in gingiva and periodontal membrane tissues is about 1 hour, and the volume of the tissue defect such as an extraction socket is about 1 $cm^3$. Therefore, when the dental preparation containing bromfenac is used as the filling or the coating material for a tissue defect, it can be said that in the drug elution profile, suitably, bromfenac is rapidly released at a release rate of 3.6 µg/hour or more until at least 3 hours after application to the tissue defect, and bromfenac is continuously released at a release rate of 0.36 µg/hour or more for at least 7 days after application. Here, the release rate of bromfenac of 3.6 µg/hour or more is a release rate estimated to be necessary to achieve the concentration of bromfenac in the tissue defect to 10 times or more of the amount of $EC_{50}$. The release rate of bromfenac of 0.36 µg/hour or more is a release rate estimated to be necessary to achieve the concentration of bromfenac in the tissue defect to $EC_{50}$ or more. Meanwhile, the present inventor has found that, in one aspect of the shaped body obtained by drying a raw material aqueous solution to which collagen and/or gelatin (A), a free form and/or alkali metal salt of bromfenac (B), and a water-soluble divalent metal salt (C) are added, the above drug release profile can be achieved, and the pain of the tissue defect in the dental field can be effectively alleviated.

It is considered that in the aqueous solution, the free form and/or alkali metal salt of bromfenac is ion-exchanged with a divalent metal ion to be converted into a divalent metal salt of bromfenac. Therefore, in the raw material aqueous solution, a part of the free form and/or alkali metal salt of bromfenac (B) added is ion-exchanged with a divalent metal ion derived from the water-soluble divalent metal salt (C) to be converted into a divalent metal salt of bromfenac. The shaped body obtained by drying the raw material aqueous solution is considered to contain the free form and/or alkali metal salt of bromfenac, and the divalent metal salt of bromfenac. For example, as one embodiment, it is considered that in the shaped body obtained by drying the raw material aqueous solution, the above drug release profile can be achieved by a structure in which the above mixed salts are supported on collagen and/or gelatin.

A shaped body in which a free form and/or alkali metal salt of bromfenac is simply supported in a matrix formed of collagen and/or gelatin tends to be disintegrated within 7 days after application into a tissue defect, and therefore its shape cannot be maintained. Meanwhile, the present inventor has found that a shaped body obtained by drying a raw material aqueous solution to which collagen and/or gelatin (A), a free form and/or alkali metal salt of bromfenac (B), and a water-soluble divalent metal salt (C) are added can stably maintain its shape even 7 days after application into a tissue defect, and can sufficiently function as a scaffold for tissue regeneration.

That is, according to an embodiment of the present disclosure, there is provided a dental preparation containing a shaped body obtained by drying a raw material aqueous solution to which collagen and/or gelatin (A), a free form and/or alkali metal salt of bromfenac (B), and a water-soluble divalent metal salt (C) are added. Hereinafter, the dental preparation of the present disclosure will be described in detail.

[Raw Material Aqueous Solution]

The raw material aqueous solution is an aqueous solution to which collagen and/or gelatin (A), bromfenac and/or an alkali metal salt (B), and a water-soluble divalent metal salt (C) are added. The raw material aqueous solution may be in a suspension state, a colloid state, or a slurry state depending on the addition amounts of components and preparation conditions, but includes all of these.

(A) Collagen and/or Gelatin

The collagen and/or gelatin added to the raw material aqueous solution serves as a matrix base material that forms the three-dimensional structure of the shaped body.

Specific examples of the collagen include telocollagen, atelocollagen, acid-soluble collagen, alkali-extracted collagen, enzyme-solubilized collagen, insoluble collagen, and derivatives and precursors thereof. Examples of the derivatives of collagen include chemically modified collagens such as acylated collagen, succinylated collagen, and alkylated collagen (for example, methylated collagen or ethylated collagen or the like). Examples of the precursors of the collagens include procollagen. Suitable examples of these collagens include atelocollagen. These collagens may be used alone, or may be used in combination of two or more thereof.

The type of the collagen may be any of type I, type II, type III, type IV, type V, type VI, type VII, type VIII, type IX, type X, type XI, type XV, and type XVII and the like, and may be a combination of two or more types. Among these types, type I and type III are preferable, and type I is more preferable.

The origin of the collagen is not particularly limited, and examples thereof include dermis, tendon, peritoneum, pericardium, cornea, vitreous body, muscle, cartilage, basement membrane, amniotic membrane of animals (porcine, bovine, chicken, and the like), fish skin, fish scales, and the like. In the present disclosure, collagen derived from one kind may be used alone, or collagens derived from two or more kinds may be used in combination. Among these, preferable examples thereof include collagen derived from animal dermis, more preferably porcine dermis or bovine dermis, and still more preferably porcine dermis.

Among these collagens, from the viewpoint of suitably having moldability and a property of stably maintaining the shape after application to the tissue defect, animal dermis-derived type I atelocollagen and animal dermis-derived type III atelocollagen are preferable, porcine dermis-derived type I atelocollagen, bovine dermis-derived type I atelocollagen, and bovine dermis-derived type III atelocollagen are more preferable, and porcine dermis-derived type I atelocollagen is still more preferable.

Specific examples of the gelatin include alkali-treated gelatin, acid-treated gelatin, and derivatives thereof. Examples of the gelatin derivatives include cationized gelatin and succinylated gelatin. These gelatins may be used alone, or may be used in combination of two or more thereof. The kind of the animal from which gelatin used in the present disclosure is derived is not particularly limited, and examples thereof include dermis, tendon, peritoneum, pericardium, cornea, vitreous body, muscle, cartilage, basement membrane, amniotic membrane of animals (porcine, bovine, chicken, and the like), fish skin, fish scales, and the like.

In the dental preparation of the present disclosure, either one of collagen and gelatin may be used alone, or a combination thereof may be used.

The amount of the collagen and/or gelatin added in the raw material aqueous solution may be appropriately set according to the amount of the collagen and/or gelatin contained in the shaped body, and is, for example, about 0.01 to 3 w/v %, preferably about 0.1 to 2.5 w/v %, and more preferably about 0.25 to 2 w/v %.

(B) Free Form and/or Alkali Metal Salt of Bromfenac

In the raw material aqueous solution, a part of the free form and/or alkali metal salt of bromfenac added is ion-exchanged with a divalent metal ion derived from a water-soluble divalent metal salt to be converted into a divalent metal salt of bromfenac. For example, when a free form of bromfenac is added to the raw material aqueous solution, a carboxyl group of bromfenac is ion-exchanged by a divalent metal ion derived from a water-soluble divalent metal salt to form a divalent metal salt of bromfenac. When an alkali metal salt of bromfenac is added to the raw material aqueous solution, an alkali metal ion of bromfenac is exchanged with a divalent metal ion derived from a water-soluble divalent metal salt to form a divalent metal salt of bromfenac.

The kind of the alkali metal salt of bromfenac is not particularly limited as long as it is pharmaceutically acceptable, and examples thereof include a sodium salt and a potassium salt. Among them, a sodium salt (i.e., bromfenac sodium) is preferable. The free form and/or alkali metal salt of bromfenac may be in the form of a solvate such as a hydrate. To the raw material aqueous solution, any one of the free form and alkali metal salt of bromfenac may be added alone, or these may be added in combination. Among the free form and alkali metal salt of bromfenac, the alkali metal salt of bromfenac is preferable, and bromfenac sodium is more preferable. As the free form and/or alkali metal salt of bromfenac, those produced by known methods may be used, or those sold as reagents may be used as they are. For example, bromfenac sodium can be purchased from Sigma-Aldrich, Inc. (USA) and Sigma-Aldrich Japan G. K. (Japan) and the like.

The ratio of the collagen and/or gelatin added to the raw material aqueous solution to the free form and/or alkali metal salt of bromfenac is not particularly limited, but for example, the total amount of the free form and/or alkali metal salt of bromfenac is about 0.1 to 1000 parts by weight, about 0.1 to 100 parts by weight, about 2 to 700 parts by weight, about 5 to 400 parts by weight, about 10 to 200 parts by weight, about 20 to 180 parts by weight, about 30 to 100 parts by weight, about 2 to 95 parts by weight, about 5 to 90 parts by weight, 10 to 90 parts by weight, or about 30 to 90 parts by weight per 100 parts by weight of the total amount of the collagen and/or gelatin. With respect to the ratio of collagen and/or gelatin to free and/or alkali metal salt of bromfenac added to the aqueous raw material solution, the amount of the free form and/or alkali metal salt of bromfenac is preferably about 2 to 700 parts by weight, more preferably about 5 to 400 parts by weight, still more preferably about 10 to 200 parts by weight, particularly preferably about 20 to 180 parts by weight, and most preferably about 30 to 100 parts by weight per 100 parts by weight of the collagen and/or gelatin.

The amount of the free form and/or alkali metal salt of bromfenac added in the raw material aqueous solution may be appropriately set according to the amount of bromfenac contained in the shaped body, and is, for example, about 0.01 to 10 w/v %, about 0.03 to 5 w/v %, about 0.05 to 3.5 w/v %, about 0.01 to 2 w/v %, about 0.1 to 2 w/v %, about 0.1 to 1.5 w/v %, about 0.2 to 1.5 w/v %, about 0.2 to 1.2 w/v %, about 0.3 to 1.2 w/v %, or 0.3 to 1.1 w/v %. The amount of the free form and/or alkali metal salt of bromfenac added in the raw material aqueous solution is preferably about 0.03 to 5 w/v %, more preferably about 0.05 to 3.5 w/v %, still more preferably about 0.1 to 2 w/v %, particularly preferably about 0.2 to 1.5 w/v %, and most preferably about 0.3 to 1.2 w/v %. As described above, in the raw material aqueous solution, a part of the free form and/or alkali metal salt of bromfenac added is converted into the divalent metal salt of bromfenac, but the addition amount of the free form and/or alkali metal salt of bromfenac described here is the amount of the free form and/or alkali metal salt of bromfenac added to the raw material aqueous solution, and is not the amount of substance present as the free form and/or alkali metal salt of bromfenac in the raw material aqueous solution.

(C) Water-Soluble Divalent Metal Salt

In the raw material aqueous solution, at least some of divalent metal ions of the water-soluble divalent metal salt added are ion-exchanged with the free form and/or alkali metal salt of bromfenac to produce a divalent metal salt of bromfenac. The water-soluble divalent metal salt added to the raw material aqueous solution plays a role of controlling the release rate of bromfenac after application to the tissue defect and improving the storage stability of bromfenac.

The kind of the water-soluble divalent metal salt is not particularly limited as long as it is pharmaceutically acceptable, and examples thereof include a water-soluble calcium salt, a water-soluble magnesium salt, a water-soluble zinc salt, and the like. The water-soluble divalent metal salt may be a halide such as chloride or bromide; an inorganic acid salt such as sulfate, sulfite, hydrogen sulfate, thiosulfate, lauryl sulfate, nitrate, edetate, sorbate, acetate, cyanide, tetraborate, permanganate, carbonate, hydrogen carbonate, oxide, hydroxide, stearate, silicate, polycarbophil, iodide, fluoride, peroxide, nitride, hypochlorite, chlorite, or perchlorate; or an organic acid salt such as gluconate, tartrate, acetate, lactate, alginate, citrate, phosphate, hydrogen phosphate, malate, phthalate, fumarate, propionate, saccharate, pyrophosphate, benzoate, or formate. Specific examples of the water-soluble divalent metal salt include calcium chloride, calcium tetraborate, calcium acetate, calcium citrate, calcium thiosulfate, calcium sulfate, calcium gluconate, calcium chlorate, magnesium phosphate, magnesium hydrogen carbonate, magnesium thiosulfate, magnesium chloride, magnesium sulfate, magnesium acetate, magnesium benzoate, zinc sulfate, zinc chloride, zinc bromide, zinc nitrate, zinc phosphate, and the like. The water-soluble divalent metal salt may be in the form of a solvate such as a hydrate. These water-soluble divalent metal salts may be used alone, or may be used in combination of two or more thereof. From the viewpoint of achieving a more suitable drug release profile, the water-soluble divalent metal salt is preferably a halide of a divalent metal or a sulfate of a divalent metal; more preferably calcium chloride, calcium acetate, calcium citrate, magnesium chloride, magnesium acetate, zinc chloride, zinc sulfate; still more preferably calcium chloride, calcium acetate, magnesium chloride, magnesium acetate, zinc chloride, zinc sulfate; and most preferably calcium chloride.

In the raw material aqueous solution, as the ratio of the water-soluble divalent metal salt to be added to the free form and/or alkali metal salt of bromfenac to be added increases, the production amount of the divalent metal salt of bromfenac increases, and therefore the persistence of release of bromfenac tends to increase, and the release rate of bromfenac until 3 hours after application of the tissue defect tends to decrease. In the raw material aqueous solution, as the ratio of the water-soluble divalent metal salt to be added to the free form and/or alkali metal salt of bromfenac to be added decreases, the production amount of the divalent metal salt of bromfenac decreases, and therefore the persistence of release of bromfenac tends to decrease, and the release rate of bromfenac until 3 hours after application of the tissue defect tends to increase. Therefore, it is desirable that the addition amount of the water-soluble divalent metal salt to the raw material aqueous solution is set so as to have a desired drug release profile according to the addition amount of the free form and/or alkali metal salt of bromfenac, and the kind of the water-soluble divalent metal salt to be used, and the like.

For example, the addition amount of the water-soluble divalent metal salt may be adjusted so as to satisfy a ratio of about 0.01 to 5 Eq, preferably about 0.02 to 4.5 Eq, more preferably about 0.03 to 4 Eq, and still more preferably about 0.05 to 3 Eq, particularly preferably about 0.3 to 1.7 Eq, and most preferably about 1.3 to 1.7 Eq as an equivalent in terms of divalent metal atom of the water-soluble divalent metal salt per 1 Eq as an equivalent in terms of free form of the free form and/or alkali metal salt of bromfenac added in the raw material aqueous solution. By satisfying such a ratio, the release rate of bromfenac is high until at least 3 hours after application to the tissue defect, and bromfenac can be continuously released for 7 days after application.

As described above, for the dental preparation applied to the tissue defect, it is suitable to have a drug elution profile (hereinafter, may be abbreviated as "drug release profile A") rapidly releasing bromfenac at a release rate of 3.6 µg/hour or more until at least 3 hours after application, and continuously releasing bromfenac at a release rate of 0.36 µg/hour or more for at least 7 days after application. In one aspect of the dental preparation of the present disclosure, the drug release profile A can be achieved by adjusting the ratio of the water-soluble divalent metal salt to the free form and/or alkali metal salt of bromfenac to be added to the raw material aqueous solution.

More specifically, in order to achieve the drug release profile A using a water-soluble calcium salt as the water-soluble divalent metal salt, for example, in a raw material aqueous solution, the addition amount of the water-soluble calcium salt may be adjusted so as to satisfy a ratio of about 0.01 to 5 Eq, preferably about 0.05 to 4 Eq, more preferably about 0.1 to 3 Eq, still more preferably about 0.2 to 2 Eq, and most preferably about 0.3 to 1.5 Eq or about 0.3 to 1.7 Eq as an equivalent in terms of calcium atom of the water-soluble calcium salt per 1 Eq as an equivalent in terms of free form of the free form and/or alkali metal salt of bromfenac added. When 0.2 to 2 Eq is satisfied as an equivalent in terms of calcium atom of the water-soluble calcium salt per 1 Eq as an equivalent in terms of free form of the free form and/or alkali metal salt of bromfenac, an effect of stably maintaining the shape of the shaped body after application to the tissue defect can be enhanced. In particular, when 0.5 to 1.7 Eq, 0.5 to 1.3 Eq or 0.5 to 0.8 Eq is satisfied as an equivalent in terms of calcium atom of the water-soluble calcium salt per 1 Eq as an equivalent in terms of free form of the free form and/or alkali metal salt of bromfenac, the effect of stably maintaining the shape of the shaped body after application to the tissue defect can be further enhanced. When 0.5 to 1.7 Eq, 1.0 to 1.7 Eq, or 1.3 to 1.7 Eq is satisfied as an equivalent in terms of calcium atom of the water-soluble calcium salt per 1 Eq as an equivalent in terms of free form of the free form and/or alkali metal salt of bromfenac, the effect of continuously releasing bromfenac after application into the tissue defect can be further enhanced.

In order to achieve the drug release profile A using the water-soluble magnesium salt as the water-soluble divalent metal salt, for example, in the raw material aqueous solution, the addition amount of the water-soluble magnesium salt may be adjusted so as to satisfy a ratio of about 0.01 to 5 Eq, preferably about 0.1 to 4 Eq, and more preferably about 0.3 to 3 Eq as an equivalent in terms of magnesium atom of the water-soluble magnesium salt per 1 Eq as an equivalent in terms of free form of the free form and/or alkali metal salt of bromfenac added.

In order to achieve the drug release profile A using the water-soluble zinc salt as the water-soluble divalent metal salt, for example, in the raw material aqueous solution, the addition amount of the water-soluble zinc salt may be adjusted so as to satisfy a ratio of about 0.01 to 5 Eq, preferably about 0.1 to 4 Eq, and more preferably about 0.3 to 3 Eq as an equivalent in terms of zinc atom of the water-soluble zinc salt per 1 Eq as an equivalent in terms of free form of the free form and/or alkali metal salt of bromfenac added.

Other Components

In addition to the above components, other pharmacological component and/or additive may be added to the raw material aqueous solution as necessary. The pharmacological component and/or additive added to the raw material aqueous solution remains in the shaped body, and can be contained in the dental preparation of the present disclosure.

Specific examples of the pharmacological component include an antibacterial agent, an antibiotic, a blood circulation improving agent, a steroid drug, a bone morphogenetic protein, a fibroblast growth factor, a transforming growth factor, an insulin-like growth factor, a platelet-derived growth factor, a vascular endothelial growth factor, a hemostatic agent, a plasma concentrate, various vitamins, and the like.

Specific examples of the additive include a buffer, a stabilizer, a dispersant (suspending agent), a pH adjusting agent, an antioxidant, an isotonizing agent, a thickening agent, a plasticizer, a sweetening agent, a flavoring agent, a preservative, a coating agent, a disintegrating agent, a foaming agent, and the like.

pH

The pH of the raw material aqueous solution may be appropriately adjusted within a range in which collagen and/or gelatin (A), a free form and/or alkali metal salt of bromfenac (B), and a water-soluble divalent metal salt (C) can be dissolved, and is, for example, about pH 3 to 10, preferably about pH 4 to 9.6, more preferably about pH 4.5 to 9.3, and still more preferably about pH 5 to 9. The pH of the raw material aqueous solution can be adjusted using a pH adjusting agent.

Method for Preparing Raw Material Aqueous Solution

The raw material aqueous solution is prepared by adding collagen and/or gelatin (A), a free form and/or alkali metal salt of bromfenac (B), a water-soluble divalent metal salt (C), and other pharmacological component and/or additive as necessary to purified water, followed by dissolving. A method for preparing the raw material aqueous solution is not particularly limited, and examples thereof include a method for preparing an aqueous solution A obtained by adding and dissolving collagen and/or gelatin (A) in purified water, and an aqueous solution B obtained by adding and dissolving a free form and/or alkali metal salt of bromfenac (B) and a water-soluble divalent metal salt (C) in purified water, and mixing predetermined amounts of the aqueous solution A and the aqueous solution B. Other pharmacological component and/or additive to be added as necessary may be added to either the aqueous solution A or the aqueous solution B. When collagens are dissolved, some of the collagens are also dissolved in an aqueous solution in a neutral pH region, but the dissolution of the collagens can be promoted by adjusting the pH of the aqueous solution to be acidic. Heating can also be performed when the collagen and gelatin are dissolved.

[Shaped Body]

The dental preparation of the present disclosure contains a shaped body obtained by drying the raw material aqueous solution.

In order to obtain the shaped body by drying the raw material aqueous solution, a known method such as freeze drying or drying under atmospheric pressure can be performed. If necessary, before the raw material aqueous solution is dried, the collagen and/or gelatin may be subjected to a crosslinking treatment by a heat treatment, addition of a crosslinking agent, an ultraviolet treatment, or an electron beam treatment or the like.

When the raw material aqueous solution is dried, a shaped body in which components other than the collagen and/or gelatin in the aqueous solution is supported on a three-dimensional structure of a matrix formed of the collagen and/or gelatin is obtained. That is, the shaped body used in the dental preparation of the present disclosure may be a three-dimensional structure in which a free form and/or alkali metal salt of bromfenac, a divalent metal salt of bromfenac, and other pharmacological component and/or additive added as necessary are supported on a matrix formed of collagen and/or gelatin. The divalent metal salt of bromfenac that may be contained in the shaped body is a salt of a divalent metal derived from the water-soluble divalent metal salt added to the raw material aqueous solution and bromfenac, and for example, when a water-soluble calcium salt is added to the raw material aqueous solution, the divalent metal salt of bromfenac that may be contained in the shaped body is a calcium salt of bromfenac.

The content of the collagen and/or gelatin in the shaped body depends on the amount of the collagen and/or gelatin added to the raw material aqueous solution, and for example, the content of the collagen and/or gelatin per 1 g of the shaped body is about 10 to 990 mg, preferably about 50 to 900 mg, more preferably about 100 to 800 mg, still more preferably about 150 to 750 mg, and particularly preferably about 350 to 650 mg.

The content of bromfenac in the shaped body depends on the amounts of the free form and/or alkali metal salt of bromfenac and the water-soluble divalent metal salt added to the raw material aqueous solution, and is, for example, about 1 to 800 mg or about 10 to 800 mg, preferably about 15 to 750 mg, more preferably about 20 to 700 mg, still more preferably about 25 to 650 mg, particularly preferably about 30 to 600 mg, and most preferably about 100 to 600 mg or about 300 to 600 mg as an amount of bromfenac in terms of free form per 1 g of the shaped body. For example, the amount of bromfenac in terms of a free form is about 0.01 to 50 mg or about 0.1 to 40 mg, preferably about 0.2 to 34.44 mg, more preferably about 0.2 to 12 mg, and still more preferably about 2 to 10 mg per shaped body. Here, the content of bromfenac in the shaped body is the total amount of the free form of bromfenac, the alkali metal salt thereof, and the divalent metal salt thereof in the shaped body.

The shape of the shaped body may be any shape that can be filled into the tissue defect, and examples thereof include a block shape, a granular shape, a particle shape, a sheet shape, and a film shape. Specific examples of the block shape include a bullet shape (a cylindrical shape in which one apex portion forms a curved surface having a hemispherical shape or a semi-elliptical shape, or the like), a cylindrical shape, a disk shape, a ball shape, and an elliptical ball shape. Among these shapes, a block shape, and preferably a bullet shape or a cylindrical shape is exemplified. Above all, a shaped body having a bullet shape is easily filled into a tissue defect such as an extraction socket, and is particularly preferable from the viewpoint of easy implantation.

When the shaped body has a bullet shape or a cylindrical shape, the weight per shaped body is, for example, about 5 to 300 mg, preferably about 10 to 250 mg, more preferably about 15 to 200 mg, and still more preferably about 20 to 150 mg. When the shaped body has a bullet shape or a cylindrical shape, the height of the shaped body (the length of the shaped body in a major axis direction) is about 5 to 50 mm, preferably about 6 to 40 mm, more preferably about 7 to 35 mm, and still more preferably about 8 to 30 mm, and the diameter of the shaped body (in the case of a bullet shape, the diameter of a cylindrical portion) is about 4 to 20 mm, preferably about 5 to 18 mm, more preferably about 6 to 16 mm, and still preferably about 7 to 15 mm.

When the shaped body has a sheet shape, the weight per shaped body is, for example, about 5 to 500 mg, preferably about 10 to 400 mg, more preferably about 15 to 300 mg, and still more preferably about 20 to 200 mg. When the shaped body has a sheet shape, the thickness of the shaped body is about 0.1 to 50 mm, preferably about 0.3 to 40 mm, more preferably about 0.5 to 35 mm, and still more preferably about 1 to 30 mm. When the shaped body has a sheet shape, the length direction and width direction of the shaped body are each about 3 to 400 mm, preferably about 4 to 350 mm, more preferably about 5 to 300 mm, and still more preferably about 6 to 250 mm.

When the shaped body has a block shape, the density of the shaped body is, for example, about 3 to 200 $mg/cm^3$, preferably about 5 to 175 $mg/cm^3$, more preferably about 7 to 150 $mg/cm^3$, and still more preferably about 9 to 125 $mg/cm^3$.

In order to form the shaped body into a desired shape, a raw material aqueous solution may be filled into a mold corresponding to the desired shape and dried, further the obtained shaped body may be cut.

In one aspect of the dental preparation of the present disclosure, the shaped body is preferably a porous body such as a sponge-like body in order to facilitate impregnation with a body fluid when the shaped body is embedded in the tissue defect. For example, a sponge-like shaped body such as a collagen sponge or gelatin sponge shaped body can be obtained by freeze-drying the raw material solution.

Application and Method of Use

The dental preparation of the present disclosure is used for the purpose of alleviating pain, hemostasis, promotion of tissue regeneration, or prevention of infection, or the like by embedding the dental preparation in a tissue defect or coating the tissue defect with the dental preparation as a filling or a coating material for the tissue defect in a dental region. When the dental preparation of the present disclosure is applied to the tissue defect, the dental preparation can release bromfenac at a high release rate until at least 3 hours after application, and can continuously release bromfenac for at least 7 days after application, so that the dental preparation can particularly exhibit an excellent alleviating effect on pain in the tissue defect. The dental preparation of the present disclosure has both suitable effects of a drug release profile and shape-maintaining characteristics, so that the dental preparation can exhibit an excellent effect particularly for a treatment method for promoting the pain alleviation of the tissue defect. Furthermore, the dental preparation of the present disclosure can maintain the shape of the preparation for at least 7 days even after the preparation is implanted in the tissue defect, or the tissue defect is coated with the preparation. As described above, the dental preparation of the present disclosure has both suitable effects of a drug release profile and shape-maintaining characteristics, and exhibits two effects of an anti-inflammatory analgesic effect provided by the release of bromfenac and a wound protective effect, so that it is possible to perform the treatment of the tissue defect in the dental region, particularly, the treatment for promoting the pain alleviation of the tissue defect.

The type of the tissue defect to which the dental preparation of the present disclosure is applied is not particularly limited. In an embodiment of the dental preparation of the present disclosure, the tissue defect to be applied is a tissue defect involving inflammation. In an embodiment of the dental preparation of the present disclosure, the tissue defect to be applied is an extraction socket. In one aspect of the dental preparation of the present disclosure, the tissue defect to be applied includes a periodontal tissue defect to which a guided bone regeneration method or a guided tissue regeneration method is applied in a dental region.

The amount of the dental preparation of the present disclosure applied to the tissue defect may be appropriately set according to the size of the tissue defect, and is, for example, about 5 to 300 mg, preferably about 10 to 250 mg, more preferably about 15 to 200 mg, and still more preferably about 20 to 150 mg in terms of the weight of the shaped body. Another example of the amount of the dental preparation of the present disclosure applied to the tissue defect is about 25.9 μg to 32 mg or about 70.2 μg to 16 mg as an amount in terms of free form of bromfenac contained in the dental preparation to be applied.

After the dental preparation of the present disclosure is embedded in the tissue defect, or the tissue defect is coated with the dental preparation, suturing for holding the dental preparation may be performed as necessary. When the dental preparation of the present disclosure is embedded in the tissue defect, followed by suturing, the release persistence of bromfenac can be further improved by suturing with a primary closure method. In the present disclosure, the primary closure method is a method for suturing a wound portion filled with a dental preparation such that no gap is present.

4. Dental Preparation (2)

The above-mentioned shaped body contains a free form and/or alkali metal salt of bromfenac and a divalent metal salt of bromfenac in a matrix formed of collagen and/or gelatin. Based on the characteristics of the shaped body, the release rate of bromfenac is high until at least 3 hours after application to a tissue defect, and bromfenac can be continuously released for at least 7 days after application. That is, in another embodiment of the present disclosure, there is provided a dental preparation containing a free form and/or alkali metal salt of bromfenac and a divalent metal salt of bromfenac in a matrix formed of collagen and/or gelatin. In the dental preparation, the alkali metal salt of bromfenac, the divalent metal salt of bromfenac, the composition, the shape, and the application and the like are as described in the section of "1. Dental Preparation (1)" above. The dental preparation can be produced by the same method as that of the shaped body described in the section of "1. Dental Preparation (1)", but is not limited thereto.

EXAMPLES

Hereinafter, the present invention will be specifically described with reference to Examples, but the present invention is not limited thereto at all.

Test Example 1

1. Production of Bullet-Shaped Collagen Sponge Preparation

Collagen (bovine dermis-derived type I atelocollagen, KOKEN CO., LTD. (Japan), manufacturer product number CLP-01) was immersed in water. An appropriate amount of 1 mol/L hydrochloric acid was then added thereto, followed by stirring to obtain a solution A in which 1.5 w/v % of collagen was dissolved. Separately, a specified amount of bromfenac sodium 1.5 hydrate (manufactured by Regis Technologies, Inc.), Trometamol (manufactured by KANTO CHEMICAL CO., INC.), and a water-soluble metal salt (calcium chloride dihydrate: manufactured by Tomita Pharmaceutical Co., Ltd., zinc sulfate heptahydrate: manufactured by Merck KGaA, aluminum chloride hexahydrate: manufactured by FUJIFILM Wako Pure Chemical Corporation) were weighed, and mixed with an appropriate amount of purified water. Then, the pH of the mixture was adjusted to about 8 to obtain a solution B. A raw material aqueous solution was obtained by mixing the solution A and the solution B in such a manner that the amounts of components per collagen sponge preparation shown in Tables 1 to 3 were adjusted so as to be contained in 1 mL of purified water. A round-bottom 2 mL polypropylene container was filled with 1 mL of the obtained raw material aqueous solution. The container was frozen at −30° C. overnight, and then freeze-dried to obtain a bullet-shaped collagen sponge preparation (bullet-shaped sponge-like shaped body, diameter of cylindrical portion: about 10 mm, height: about 20 mm).

2. Method for Evaluating Bromfenac Release Characteristics and Shape-Maintaining Characteristics One collagen sponge preparation was placed in a 5 mL polypropylene tube, and 1 mL of PBS (−) was further placed as a release liquid. The polypropylene tube was capped, and immediately placed in a shaker (50 rpm) heated to 37° C. This time point was defined as a release time of 0 hours (t=0). With time, the supernatant in the polypropylene tube was sampled. At the time of sampling, 0.5 mL of the supernatant in the polypropylene tube was sampled. The same amount of PBS (−) was immediately added to the polypropylene tube, and the polypropylene tube was returned to a shaker (50 rpm) heated to 37° C. The concentration of bromfenac in the sampled supernatant was measured by high performance liquid chromatography (HPLC), and the release amount (µg/h) of bromfenac per unit time was determined according to the following formula.

Release amount of bromfenac per unit time (µg/h) = [Expression 1]

$$\{[(M_n \times 1) - [M_{n-1} \times (1 - 0.5)]]\}/(t_n - t_{n-1})$$

$M_n$: Concentration of bromfenac sodium 1.5 hydrate in supernatant sampled on n-th try (µg/mL)
$M_{n-1}$: Concentration of bromfenac sodium 1.5 hydrate in supernatant sampled on (n−1)-th try (µg/mL)
$t_n$: Time of sampling on n-th try
$t_{n-1}$: Time of sampling on (n−1)-th try
Note that in calculation of release amount of bromfenac per unit time at time of first sampling, $M_{n-1}$ is 0 µg/mL, and $t_{n-1}$ is 0 hour From the measurement results of the release amount of bromfenac per unit time at each sampling time, the release characteristics of bromfenac were evaluated according to the following criteria.

<Evaluation of Release Characteristics of Bromfenac>
a: "The release amount of bromfenac per unit time until a release time of 3 hours is 3.6 µg/hour or more, and the release amount of bromfenac per unit time is maintained at 0.36 µg/hour or more until a release time of about 168 hours." is satisfied.
b: "The release amount of bromfenac per unit time until a release time of 3 hours is 3.6 µg/hour or more, and the release amount of bromfenac per unit time is maintained at 0.36 µg/hour or more until a release time of about 168 hours." is not satisfied.

The appearance of the collagen sponge preparation was observed at the release times of 0 hours and 168 hours, and a photograph of the collagen sponge preparation was taken to measure the image area of the collagen sponge preparation from the photograph. The elasticity of the collagen sponge preparation pressed with a glass rod or the like was confirmed, and the shape-maintaining characteristics of the collagen sponge preparation were evaluated according to the following criteria.

<Evaluation Due to Appearance Observation (Including Elasticity)>
1: The collagen sponge preparation is not disintegrated, and has sufficient elasticity (repulsion properties when pushed).
2: The collagen sponge preparation is not disintegrated, but has insufficient elasticity.
3: The collagen sponge preparation is disintegrated.

<Evaluation Using Image Area>
1: The image area at the release time of 168 hours is 50% or more with respect to the image area at the release time of 0 hours.
2: The image area at the release time of 168 hours is 10% or more and less than 50% with respect to the image area at the release time of 0 hours.
3: The image area at the release time of 168 hours is less than 10% with respect to the image area at the release time of 0 hours.

—: The collagen sponge preparation is disintegrated at the release time of 168 hours, and the image area cannot be obtained.

<Comprehensive Evaluation>

A: Both the evaluation based on the appearance (including elasticity) and the evaluation of the image area are 1.

B: One of the evaluations based on the appearance (including elasticity) or the image area is 1, and the other is 2.

C: Both the evaluation based on the appearance (including elasticity) and the evaluation using the image area are 2.

D: At least one of the evaluations based on the appearance (including elasticity) or the evaluation using the image area is 3 or —.

3. Results

Figure 2:
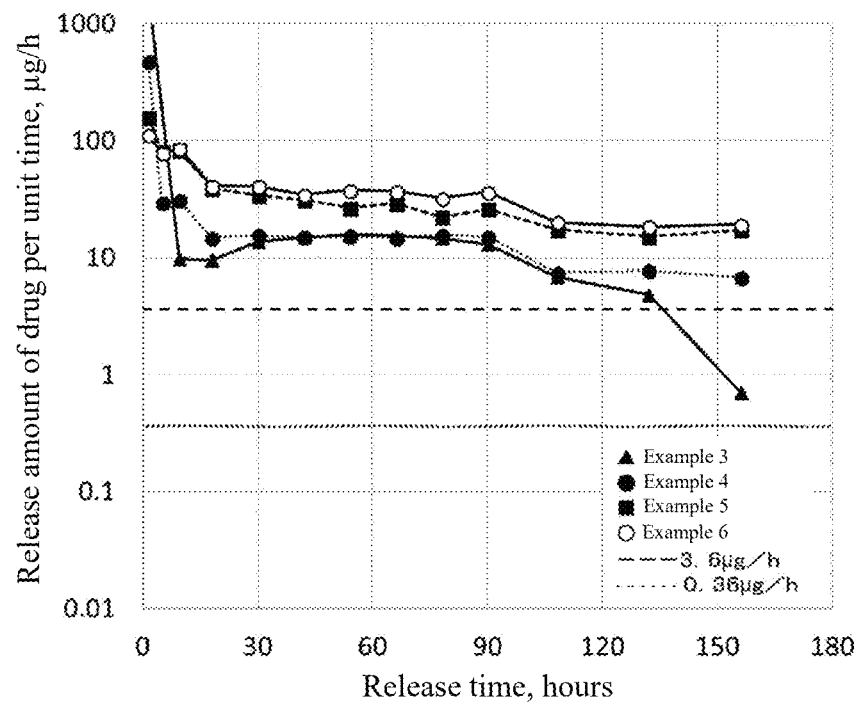
FIG. 2 is a view showing a temporal change in the release amount of bromfenac per unit time for a collagen sponge preparation of each of Examples 3 to 6.
Figure 3:
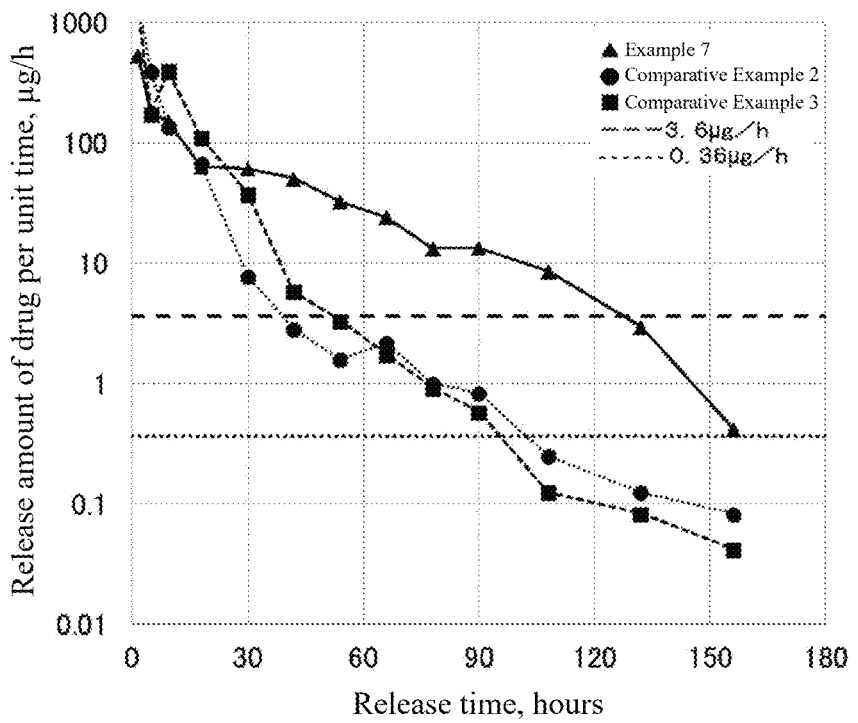
FIG. 3 is a view showing a temporal change in the release amount of bromfenac per unit time for a collagen sponge preparation of each of Example 7 and Comparative Examples 2 and 3.
Figure 4:
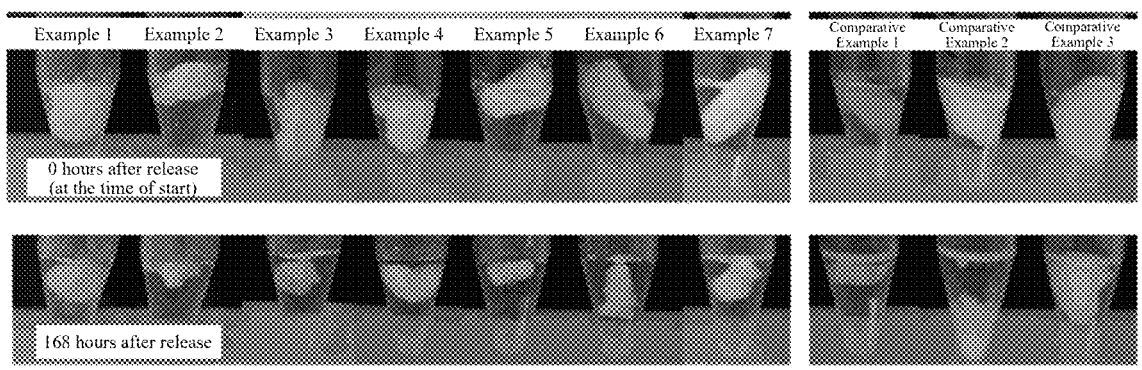
FIG. 4 shows the photograph of the collagen sponge preparation of each of Examples 1 to 7 and Comparative Examples 1 to 3 when shape-maintaining characteristics are evaluated.

The obtained results are shown in Tables 1 to 3. FIGS. 1 to 3 show a temporal change in the release amount (μg/h) of bromfenac per unit time, and FIG. 4 shows the photographs of the appearances of the collagen sponge preparation taken at the release times of 0 hours and 168 hours.

In the collagen sponge preparation (Comparative Example 1) formed using the raw material aqueous solution to which collagen and bromfenac sodium 1.5 hydrate were added, the release rate of bromfenac until the release time of 3 hours was 3.6 μg/hour or more, and bromfenac could be rapidly released, but when the release time was more than 52 hours, the release rate of bromfenac was lower than the release rate of 0.36 μg/hour or more. In the collagen sponge preparation of Comparative Example 1, the shape could not be maintained at the release time of 52 hours (when the release of bromfenac was finished) as well as at the release time of about 168 hours.

Meanwhile, in the collagen sponge preparations (Examples 1 to 6) formed using the raw material aqueous solution to which collagen, bromfenac sodium 1.5 hydrate, and calcium chloride dihydrate were added, the release rate of bromfenac was 3.6 μg/hour or more until the release time of 3 hours, and the release rate of bromfenac could be maintained at 0.36 μg/hour or more until the release time of 168 hours. The release rate of bromfenac was high until 3 hours from the start and a sufficient amount of bromfenac could be continuously released for 168 hours from the start. In Examples 1 to 6, the shape could be stably maintained even at the release time of 168 hours. Above all, the collagen sponge preparations (Examples 1 and 4) formed of the raw material aqueous solution to which calcium chloride dihydrate of 0.52 to 0.78 Eq as an equivalent in terms of calcium atom was added per 1 Eq as an equivalent in terms of free form of bromfenac sodium 1.5 hydrate had remarkably excellent shape stability at the release time of 168 hours.

The collagen sponge preparation (Example 7) obtained by using zinc sulfate heptahydrate instead of calcium chloride dihydrate had a high release rate of bromfenac until 3 hours from the start of use, could continuously release a sufficient amount of bromfenac for 7 days from the start and had good shape stability at the release time of 168 hours.

Meanwhile, the collagen sponge preparations (Comparative Examples 2 and 3) obtained using aluminum chloride hexahydrate instead of calcium chloride dihydrate had a high release rate of bromfenac until 3 hours from the start of use, but when the release time was more than 110 hours, the collagen sponge preparations had a release rate of bromfenac lower than the release rate of 0.36 μg/hour or more, and could not continuously release bromfenac.

From the above results, it has been found that a shaped body obtained by drying a raw material aqueous solution to which collagen, an alkali metal salt of bromfenac, and a water-soluble divalent metal salt are added has a high release rate of bromfenac until 3 hours from the start of use, can continuously release bromfenac for 7 days from the start of use, and has a suitable drug release profile as a dental preparation used for the treatment of a tissue defect in the dental field. In Examples 1 to 6, it is considered that a part of bromfenac sodium added to the raw material aqueous solution at the time of production is ion-exchanged with a divalent metal ion derived from a water-soluble divalent metal salt to produce a divalent metal salt of bromfenac, and the drug release profile is shown based on the fact that rapid-release bromfenac sodium and a slow-release bromfenac divalent metal salt are mixed in the collagen sponge preparation.

TABLE 1

|  |  | Examples | | Comparative Example |
|---|---|---|---|---|
|  |  | 1 | 2 | 1 |
| Bromfenac sodium 1.5 hydrate | | 8 mg | 8 mg | 8 mg |
| Calcium chloride dihydrate | | 0.8 mg | 1.6 mg | — |
| Collagen | | 10 mg | 10 mg | 10 mg |
| Trometamol | | 2.5 mg | 2.5 mg | 2.5 mg |
| Total | | 21.3 mg | 22.1 mg | 20.5 mg |
| Equivalent (Eq) in terms of calcium atom of calcium chloride dihydrate per 1 Eq as equivalent in terms of free form of bromfenac sodium 1.5 hydrate | | 0.52 | 1.04 | 0.0 |
| Release characteristics of bromfenac | | a (FIG. 1) | a (FIG. 1) | b (FIG. 1) |
| Shape-maintaining characteristics | Comprehensive evaluation | A | B | C |
| | Evaluation due to appearance observation | 1 | 1 | 2 |
| | Evaluation using image area | 1 | 2 | 2 |

In Table, the total of amounts of components is the amount per collagen sponge preparation.

TABLE 2

|  |  | Examples | | | |
| --- | --- | --- | --- | --- | --- |
|  |  | 3 | 4 | 5 | 6 |
| Bromfenac sodium 1.5 hydrate | | 8 mg | 8 mg | 8 mg | 8 mg |
| Calcium chloride dihydrate | | 0.4 mg | 1.2 mg | 2.0 mg | 2.4 mg |
| Collagen | | 10 mg | 10 mg | 10 mg | 10 mg |
| Trometamol | | 2.5 mg | 2.5 mg | 2.5 mg | 2.5 mg |
| Total | | 20.9 mg | 21.7 mg | 22.5 mg | 22.9 mg |
| Equivalent (Eq) in terms of calcium atom of calcium chloride dihydrate per 1 Eq as equivalent in terms of free form of bromfenac sodium 1.5 hydrate | | 0.26 | 0.78 | 1.30 | 1.56 |
| Release characteristics of bromfenac | | a (FIG. 2) | a (FIG. 2) | a (FIG. 2) | a (FIG. 2) |
| Shape-maintaining characteristics | Comprehensive evaluation | B | A | B | B |
| | Evaluation due to appearance observation | 1 | 1 | 1 | 1 |
| | Evaluation using image area | 2 | 1 | 2 | 2 |

In Table, the total of amounts of components is the amount per collagen sponge preparation.

TABLE 3

|  |  | Example | Comparative Examples | |
| --- | --- | --- | --- | --- |
|  |  | 7 | 2 | 3 |
| Bromfenac sodium 1.5 hydrate | | 8 mg | 8 mg | 8 mg |
| Zinc sulfate heptahydrate | | 3 mg | — | — |
| Aluminum chloride hexahydrate | | — | 1.7 mg | 3.4 mg |
| Collagen | | 10 mg | 10 mg | 10 mg |
| Trometamol | | 2.5 mg | 2.5 mg | 2.5 mg |
| Total | | 23.5 mg | 22.2 mg | 23.9 mg |
| Equivalent (Eq) in terms of zinc atom of aluminum chloride hexahydrate per 1 Eq as equivalent in terms of free form of bromfenac sodium 1.5 hydrate | | 1.00 | 1.01 | 2.02 |
| Release characteristics of bromfenac | | a (FIG. 3) | b (FIG. 3) | b (FIG. 3) |
| Shape-maintaining characteristics | Comprehensive evaluation | B | D | A |
| | Evaluation due to appearance observation | 1 | 3 | 1 |
| | Evaluation using image area | 2 | — | 1 |

In Table, the total of amounts of components is the amount per collagen sponge preparation.

Test Example 2

Collagen sponge preparations were prepared using collagens of different origins and types, and the bromfenac release characteristics and shape-maintaining characteristics of the collagen sponge preparations were evaluated. Specifically, using the collagens shown in Table 5, a bullet-shaped collagen sponge preparation (bullet-shaped sponge-like shaped body, diameter of cylindrical portion: about 10 mm, height: about 20 mm) having a composition shown in Table 4 was prepared in the same manner as in Test Example 1. For the obtained collagen sponge preparation, the release amount of bromfenac per unit time was measured in the same manner as in Test Example 1, and the bromfenac release characteristics were evaluated. Furthermore, the obtained collagen sponge preparations were evaluated for the shape-maintaining characteristics in the same manner as in Test Example 1.

TABLE 4

|  | Examples 8 to 12 |
| --- | --- |
| Bromfenac sodium 1.5 hydrate | 8 mg |
| Calcium chloride dihydrate | 1.6 mg |
| Collagen shown in Table 5 | 10 mg |
| Trometamol | 2.5 mg |
| Total | 22.1 mg |
| Equivalent (Eq) in terms of calcium atom of calcium chloride dihydrate per 1 Eq as equivalent in terms of free form of bromfenac sodium 1.5 hydrate | 1.04 |

In Table, the total of amounts of components is the amount per collagen sponge preparation.

Figure 5:
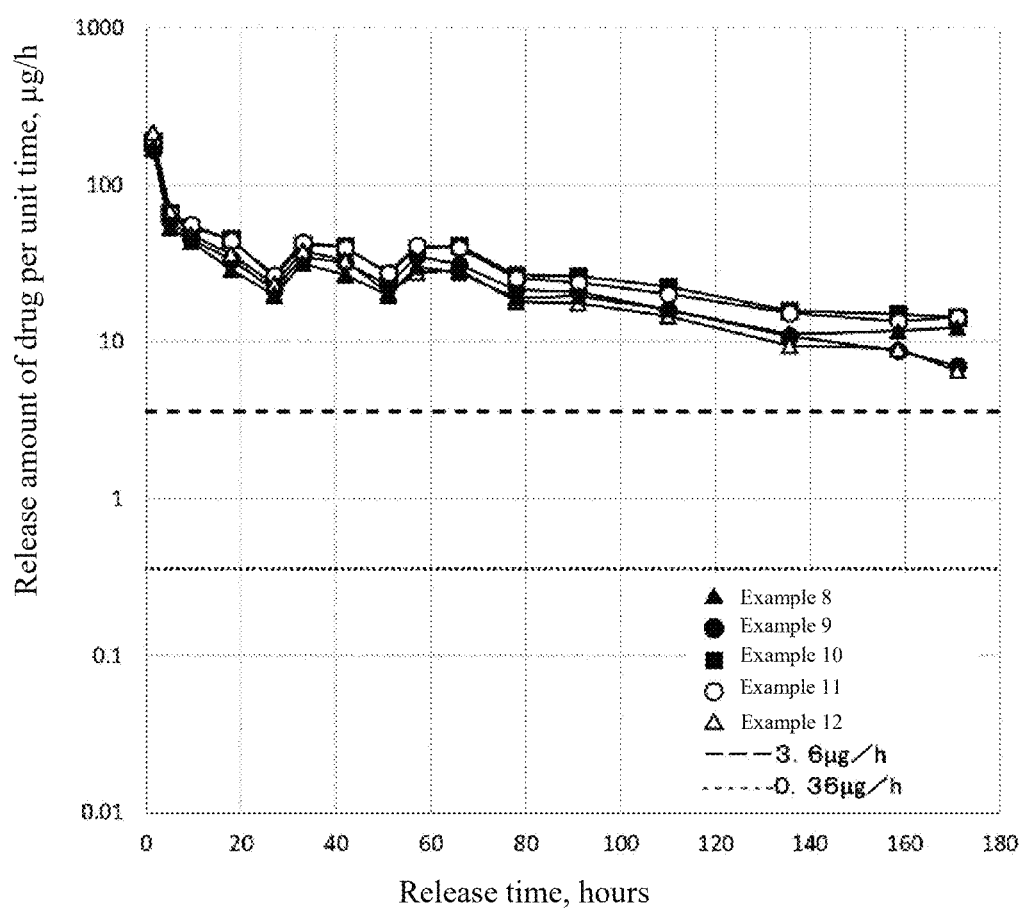
FIG. 5 is a view showing a temporal change in the release amount of bromfenac per unit time for a collagen sponge preparation of each of Examples 8 to 12.

The obtained results are shown in Table 5 and FIG. 5. As a result, it was confirmed that even when any of porcine dermis-derived type I atelocollagen, bovine dermis-derived type I atelocollagen, and bovine dermis-derived type III atelocollagen is used, the collagen sponge preparation has a high release rate of bromfenac until 3 hours from the start of use, and can have a property being capable of continuously releasing bromfenac for 7 days from the start of use. Furthermore, the obtained collagen sponge preparation could stably maintain its shape even at the release time of 168 hours.

TABLE 5

| | Collagen used | | | Release characteristics of bromfenac | Shape-maintaining characteristics | | |
|---|---|---|---|---|---|---|---|
| | Origin | Type | Brand name, manufacturer | | Comprehensive evaluation | Evaluation due to appearance observation | Evaluation using image area |
| Example 8 | Bovine dermis | Type I atelocollagen | Collagen for research CLP-01, KOKEN CO., LTD. (Japan) | a (FIG. 5) | A | 1 | 1 |
| Example 9 | Porcine dermis | Type I atelocollagen | BM-PS1047, Nitta Gelatin Inc. (Japan) | a (FIG. 5) | A | 1 | 1 |
| Example 10 | Bovine dermis | Type I atelocollagen | PSC-1-100-500PW, Nippi. Inc. (Japan) | a (FIG. 5) | B | 1 | 2 |
| Example 11 | Porcine dermis | Type I atelocollagen | PSC-1-200-500PW, Nippi Inc. (Japan) | a (FIG. 5) | A | 1 | 1 |
| Example 12 | Bovine dermis | Type III atelocollagen | PSC-3-100-05, Nippi Inc. (Japan) | a (FIG. 5) | A | 1 | 1 |

Test Example 3

Collagen sponge preparations were prepared by changing the content of bromfenac sodium 1.5 hydrate, and the bromfenac release characteristics of the collagen sponge preparations were evaluated. Specifically, a bullet-shaped collagen sponge preparations (bullet-shaped sponge-like shaped body, diameter of cylindrical portion: about 10 mm, height: about 20 mm) having compositions shown in Table 6 were prepared in the same manner as in Test Example 1. For the obtained collagen sponge preparation, the release amount of bromfenac per unit time was measured in the same manner as in Test Example 1, and the bromfenac release characteristics were evaluated. Furthermore, the obtained collagen sponge preparations were evaluated for the shape-maintaining characteristics in the same manner as in Test Example 1.

Figure 6:
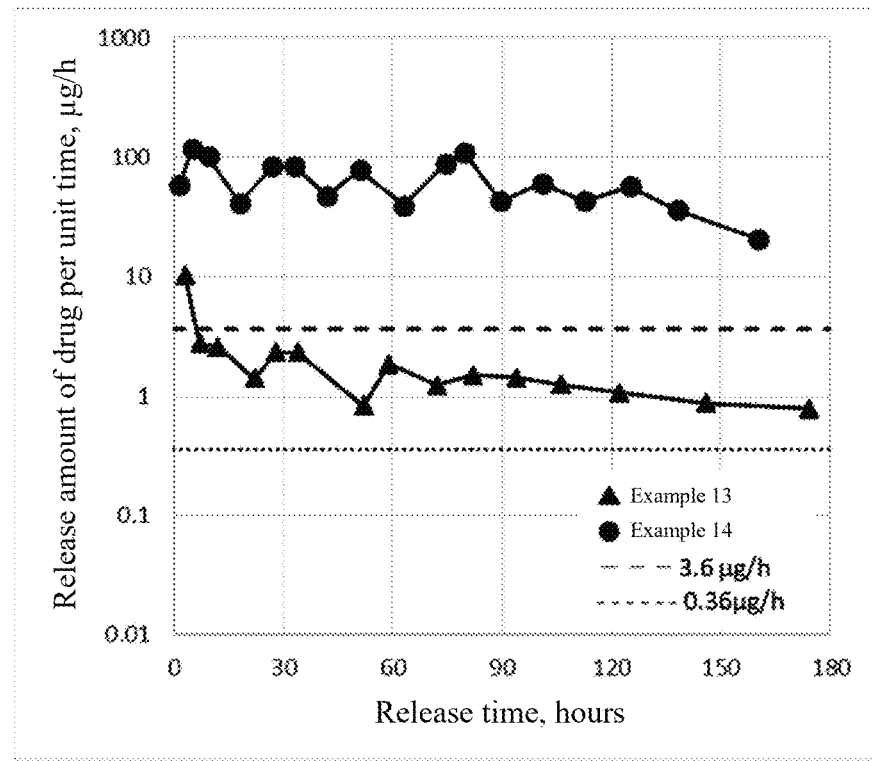
FIG. 6 is a view showing a temporal change in the release amount of bromfenac per unit time for a collagen sponge preparation of each of Examples 13 and 14.

The obtained results are shown in Table 6 and FIG. 6. As a result, it was confirmed that even when the content of bromfenac sodium 1.5 hydrate in the collagen sponge preparation is changed to 2 mg or 34.44 mg, the release rate of bromfenac was high until 3 hours from the start of use, and the collagen sponge preparation has a property of being capable of continuously releasing bromfenac for 7 days from the start of use. In any of the collagen sponge preparations, the shape thereof could be stably maintained while a sufficient amount of bromfenac was released.

TABLE 6

| | Examples | |
|---|---|---|
| | 13 | 14 |
| Bromfenac sodium 1.5 hydrate | 2 mg | 34.44 mg |
| Calcium chloride dihydrate | 0.8 mg | 8.25 mg |
| Collagen[#1] | 10 mg | 20 mg |
| Trometamol | 2.5 mg | 10 mg |
| Benzalkonium chloride[#2] | 4 mg | — |
| Stabilizer | — | Appropriate amount |
| Dispersant | — | Appropriate amount |
| Total | 19.3 mg | 78.89 mg |

TABLE 6-continued

| | | Examples | |
|---|---|---|---|
| | | 13 | 14 |
| Equivalent (Eq) in terms of calcium atom of calcium chloride dihydrate per 1 Eq as equivalent in terms of free form of bromfenac sodium 1.5 hydrate | | 2.08 | 1.25 |
| Release characteristics of bromfenac | | a (FIG. 6) | a (FIG. 6) |
| Shape-maintaining characteristics | Comprehensive evaluation | B | A |
| | Evaluation due to appearance observation | 2 | 1 |
| | Evaluation using image area | 1 | 1 |

[#1]Example 13 used bovine dermis-derived type I atelocollagen (KOKEN CO., LTD. (Japan), manufacturer product number CLP-01). Example 14 used porcine dermis-derived type I atelocollagen (Nitta Gelatin, Inc. (Japan), manufacturer product number BM-PS1047).
[#2]Benzalkonium chloride manufactured by Sigma-Aldrich Japan G.K. was used.
In Table, the total of amounts of components is the amount per collagen sponge preparation.

Test Example 4

1. Production of Bullet-Shaped Collagen Sponge Preparation

Collagen (bovine dermis-derived type I atelocollagen, KOKEN CO., LTD. (Japan), manufacturer product number CLP-01) was immersed in water. An appropriate amount of 1 mol/L hydrochloric acid was then added thereto, followed by stirring to obtain a solution A containing 1.5 w/v % of collagen. Separately, a specified amount of ibuprofen sodium (manufactured by Sigma-Aldrich Japan G. K.), Trometamol (manufactured by KANTO CHEMICAL CO., INC.), and a water-soluble metal salt (calcium chloride dihydrate: manufactured by Tomita Pharmaceutical Co., Ltd., aluminum chloride hexahydrate: manufactured by FUJIFILM Wako Pure Chemical Corporation) were weighed, and mixed with an appropriate amount of purified water. Then, the pH of the mixture was adjusted to about 8 to obtain a solution B. A raw material aqueous solution was obtained by mixing the solution A and the solution B in such a manner that the amounts of components per collagen sponge preparation shown in Table 7 were adjusted so as to be contained in 1 mL of purified water. A round-bottom 2 mL polypropylene container was filled with 1 mL of the obtained raw material aqueous solution. The container was frozen at −30° C. overnight, and then freeze-dried to obtain a bullet-shaped collagen sponge preparation (bullet-shaped sponge-like shaped body, diameter of cylindrical portion: about 10 mm, height: about 20 mm).

2. Method for Evaluating Ibuprofen Release Characteristics

The release amount of ibuprofen per unit time was measured in the same manner as in Test Example 1, and the ibuprofen release characteristics were evaluated. The concentration of ibuprofen in the sampled liquid was measured by high performance liquid chromatography (HPLC).

3. Results

Figure 7:
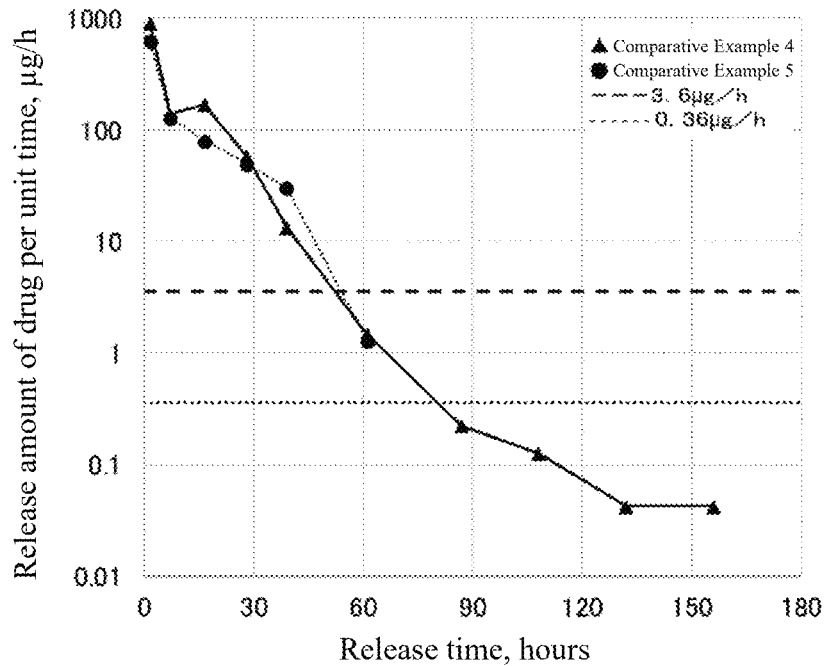
FIG. 7 is a view showing a temporal change in the release amount of ibuprofen per unit time for a collagen sponge preparation of each of Comparative Examples 4 and 5.

The obtained results are shown in Table 7. FIG. 7 shows a temporal change in the release amount (μg/h) of ibuprofen per unit time. As a result, the collagen sponge preparations (Comparative Examples 4 and 5) obtained by drying the raw material aqueous solution to which collagen, ibuprofen sodium, and a water-soluble divalent metal salt (calcium chloride dihydrate) or a water-soluble trivalent metal salt (aluminum chloride hexahydrate) were added had a high release rate of ibuprofen until the release time of 3 hours, and could rapidly release ibuprofen. However, in the collagen sponge preparation of Comparative Example 4, when the release time was more than 96 hours, the release rate was lower than the release rate of 0.36 μg/hour or more. The collagen sponge preparation of Comparative Example 5 did not release ibuprofen when the release time was more than 96 hours. That is, it was confirmed that the drug release profile observed in the collagen sponge preparations of Examples 1 to 14 is uniquely observed when bromfenac is selected as a nonsteroidal anti-inflammatory drug.

TABLE 7

| | Comparative Examples | |
|---|---|---|
| | 4 | 5 |
| Ibuprofen sodium | 8 mg | 8 mg |
| Calcium chloride dihydrate | 4 mg | — |
| Aluminum chloride hexahydrate | — | 4 mg |
| Collagen | 10 mg | 10 mg |
| Trometamol | 2.5 mg | 2.5 mg |
| Total | 24.5 mg | 24.5 mg |
| Equivalent (Eq) in terms of metal atom of water-soluble metal salt per 1 Eq as equivalent in terms of free form of ibuprofen sodium | 1.55 | 1.42 |
| Release characteristics of ibuprofen | b (FIG. 7) | b (FIG. 7) |

In Table, the total of amounts of components is the amount per collagen sponge preparation.

Test Example 5

1. Production of Bullet-Shaped Collagen Sponge Preparation

Collagen (porcine dermis-derived type I atelocollagen, manufactured by Nitta Gelatin Inc., manufacturer product number BM-PS 1047) was immersed in water. Water was then added thereto, followed by stirring to obtain a solution A in which 1.5 w/v % of collagen was dissolved. Separately, a specified amount of bromfenac sodium 1.5 hydrate (manufactured by Regis Technologies, Inc.), Trometamol (manufactured by KANTO CHEMICAL CO., INC.), and calcium chloride dihydrate (manufactured by Tomita Pharmaceutical Co., Ltd.), a stabilizer, and a dispersant were weighed, and mixed with an appropriate amount of purified water. Then, the pH of the mixture was adjusted to about 8 to obtain a solution B. A raw material aqueous solution was obtained by mixing the solution A and the solution B in such a manner that the amounts of components per collagen sponge preparation shown in Table 8 were adjusted so as to be contained in 1 mL of purified water. A round-bottom 2 mL polypropylene container was filled with 1 mL of the obtained raw material aqueous solution. The container was frozen at −30° C. overnight, and then freeze-dried to obtain a bullet-shaped collagen sponge preparation (bullet-shaped sponge-like shaped body, diameter of cylindrical portion: about 10 mm, height: about 20 mm).

TABLE 8

| | Example 15 |
|---|---|
| Bromfenac sodium 1.5 hydrate | 8.61 mg |
| Calcium chloride dihydrate | 1.65 mg |
| Collagen | 10 mg |
| Stabilizer | Appropriate amount |
| Dispersant | Appropriate amount |
| Trometamol | 2.5 mg |
| Total | 24.06 mg |
| Equivalent (Eq) in terms of calcium atom of calcium chloride dihydrate per 1 Eq as equivalent in terms of free form of bromfenac sodium hydrate | 1.00 |

In Table, the total of amounts of components is the amount per collagen sponge preparation.

2. Method of Implantation Testing in Beagle Dogs

Four 9-11 month-old Beagle dogs (TOYO Beagle, Kitayama Laves Co., Ltd.) (individuals A to D) were divided into a 2 hour-group (individuals A and B) and a 72 hour-group (individuals C and D). Two fourth premolars (P4) of the left and right mandibles of the Beagle dog were extracted by a manual method. A collagen sponge preparation was implanted in each of the two extraction sockets, and the gingiva was sutured. One of the extraction sockets in which the collagen sponge preparations were embedded was sutured by a primary closure method, and the other was sutured by a secondary closure method. Here, the primary closure method is a method for suturing a wound portion in which the collagen sponge preparation is embedded so as not to have a gap, and the secondary closure method is a method for suturing the wound portion in which the collagen sponge preparation is embedded so as to have a gap of 2 to 4 mm. The suture conditions for the beagle dogs are shown in Table 9. However, actually, in the individual C in the 72 hour-group, the suture by the primary closure of the extraction socket of the right fourth premolar was insufficient, and the wound portion had a large gap. The reason for this is that, in the gingival tissue around the extraction socket of the right fourth premolar in the individual C in the 72 hour-group, the gingival tissue collected for blank measurement before the administration of the collagen sponge preparation was larger than that in the other extraction socket, the collagen sponge preparation administered to the extraction socket could not be completely covered by the gingival tissue around the extraction socket, and thereby the suture condition could not be the primary closure state. Therefore, the results of the collagen sponge preparation administered to the extraction socket of the right fourth premolar in the individual C could not be appropriately compared with the results of the collagen sponge preparation administered to the other extraction socket.

TABLE 9

| | Individual | Suture conditions | |
|---|---|---|---|
| 2-hour group | A | Extraction socket of right fourth premolar | Primary closure |
| | | Extraction socket of left fourth premolar | Secondary closure |
| | B | Extraction socket of right fourth premolar | Secondary closure |
| | | Extraction socket of left fourth premolar | Primary closure |
| 72-hour group | C | Extraction socket of right fourth premolar | Primary closure |
| | | Extraction socket of left fourth premolar | Secondary closure |
| | D | Extraction socket of right fourth premolar | Secondary closure |
| | | Extraction socket of left fourth premolar | Primary closure |

Figure 8:
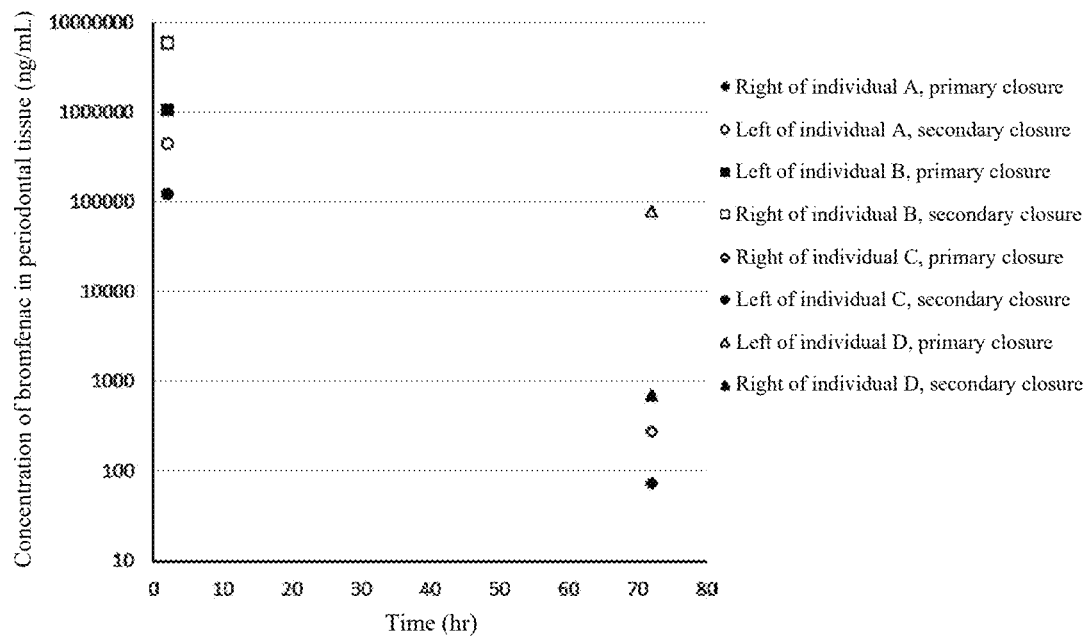
FIG. 8 is a view showing the results of implanting a collagen sponge preparation of Example 15 in each of the extraction sockets of the left and right fourth premolars of a Beagle dog and measuring the concentration of bromfenac at 2 hours or 72 hours after the administration in a gingival tissue around a site where the collagen sponge preparation is implanted.

The implantation of the collagen sponge preparation was performed only once, and the implantation time was defined as 0 hours. In the 2-hour group, the individuals were euthanized by design after 2 hours, and the gingival tissues (buccal and lingual) of the site implanted with the collagen sponge preparation were collected. In the 72-hour group, the individuals were euthanized by design after 72 hours, and the gingival tissues were collected in the same manner. The concentration of bromfenac in the collected gingival tissue was determined by an internal standard method using LC-MS/MS according to the following conditions.
<Measurement Conditions of Concentration of Bromfenac in Gingival Tissue>
A hydrous methanol solution (volume ratio of methanol: water is 1:1) was mixed with the gingival tissue and homogenized to prepare a gingival homogenate. An appropriate amount of methanol was added to the gingival homogenate, followed by sufficiently stirring and centrifuging. The supernatant after centrifugation was collected and diluted with water to obtain a sample solution. The obtained sample solution was measured using LC-MS/MS under the following conditions.
LC Conditions
   Apparatus: ExionLC AD (SCIEX)
   Column: InertSustain C18 (2.1 mm I.D.×50 mm, 3 µm, GLSciences)
   Mobile Phase: ammonium acetate solution (solution A)/mixed solution of ammonium acetate and methanol (solution B)
   Gradient Conditions: The mobile phase A and the mobile phase B were flowed under gradient conditions capable of detecting bromfenac.
MS/MS Conditions
   Apparatus: QTRAP7500 (SCIEX)
   Scan type: MRM (Multiple Reaction Monitoring)
   Ionization mode: ESI (Electrospray ionization)
   Polarity: Positive
3. Results
The obtained results are shown in FIG. 8. As described above, in the individual C, the primary closure of the extraction socket of the right fourth premolar was incomplete, and thus the result of the right fourth molar of the individual C showed that the concentration of bromfenac released from the collagen sponge preparation into the gingival tissue could not be appropriately evaluated. In the left fourth premolar of the individual C, it is considered that since figure-eight suturing designated in the test protocol is not appropriately performed as the secondary closure suturing method, the gap of the wound portion becomes larger than expected, and bromfenac is apt to be eluted from the collagen sponge preparation into saliva, which causes the concentration to fall below $EC_{50}$ (360 ng/ml).

As can be seen from the results of the individuals A and B, 2 hours after the implantation of the collagen sponge preparation, the concentration of bromfenac in the gingival tissue was more than 10 times of $EC_{50}$ (360 ng/ml) of bromfenac, which was a concentration at which strong pain felt immediately after tooth extraction could be suppressed. In the individual D, 72 hours after the implantation of the collagen sponge preparation, the concentration of bromfenac in the gingival tissue was more than $EC_{50}$ of bromfenac under both the primary closure suture condition and the secondary closure suture condition, and the release of an effective amount of bromfenac could be maintained even after 72 hours. As can be seen from the results of the individuals A, B, and D, in the suture after the implantation of the collagen sponge preparation, the concentration of bromfenac in the gingival tissue could be maintained higher in the primary closure than in the secondary closure. This is considered to be due to the fact that bromfenac is easily eluted into saliva from the collagen sponge preparation under the secondary closure suture condition.

Test Example 6

1. Production of Bullet-Shaped Collagen Sponge Preparation
Collagen (porcine dermis-derived type I atelocollagen, manufactured by Nitta Gelatin Inc., manufacturer product number BM-PS 1047) was immersed in water. Water was then added thereto, followed by stirring to obtain a solution A in which 1.5 w/v % of collagen was dissolved. Separately, a specified amount of bromfenac sodium 1.5 hydrate (manufactured by Regis Technologies, Inc.), Trometamol (manufactured by Merck KGaA), and calcium chloride dihydrate (manufactured by Merck KGaA), a stabilizer, and a dispersant were weighed, and mixed with an appropriate amount of purified water. Then, the pH of the mixture was adjusted to about 8 to obtain a solution B. A raw material aqueous solution was obtained by mixing the solution A and the solution B in such a manner that the amounts of components per collagen sponge preparation shown in Table 10 were adjusted so as to be contained in 1 mL of purified water. A round-bottom 2 mL polypropylene container was filled with 1 mL of the obtained raw material aqueous solution. The container was frozen at −30° C. overnight, and then freeze-dried to obtain a bullet-shaped collagen sponge preparation (bullet-shaped sponge-like shaped body, diameter of cylindrical portion: about 10 mm, height: about 20 mm).

TABLE 10

| | Example 16 | Comparative Example 6 |
|---|---|---|
| Bromfenac sodium 1.5 hydrate | 9.17 mg | 9.17 mg |
| Calcium chloride dihydrate | 2.63 mg | — |
| Collagen | 10 mg | 10 mg |
| Stabilizer | Appropriate amount | Appropriate amount |
| Dispersant | Appropriate amount | Appropriate amount |
| Trometamol | 2.5 mg | 2.5 mg |
| Total | 25.6 mg | 22.97 mg |
| Equivalent (Eq) in terms of calcium atom of calcium chloride dihydrate per 1 Eq as equivalent in terms of free form of bromfenac sodium hydrate | 1.5 | — |

In Table, the total of amounts of components is the amount per collagen sponge preparation.

2. Method of Implantation Testing in Beagle Dogs
2.1. Administration of Collagen Sponge Preparation Six 15 month-old or more Beagle dogs (TOYO Beagle, Kitayama Laves Co., Ltd.) (individuals a to f) at the time of arrival were divided into 3 dogs for each of an Example 16 administration group (individuals a, b, and c) and a Comparative Example 6 administration group (individuals d, e, and f). Two fourth premolars (P4) of the left and right mandibles of the Beagle dog were extracted by a manual method. Dirt in the extraction socket was washed and excess water was removed with gauze. Under the conditions shown in Table 11, the collagen sponge preparation was implanted in one tooth extraction socket and the gingiva was sutured, and the other tooth extraction socket was sutured as it was without being implanted with the collagen sponge preparation. The suturing was performed by a primary closure method, that is, a method in which suturing is performed so that there is no gap in the wound portion in which the collagen sponge preparation is embedded. After suturing, the collagen sponge preparation was carefully disinfected so as not to be wetted. The implantation of the collagen sponge preparation was performed only once, and the implantation time was defined as 0 hours.

exudate had been wiped off was placed in a covered tube and cryopreserved at −60° C. or lower until measurement.

For blood collection, about 1.5 mL of blood was collected per one time by a manual method using a syringe. Sodium heparin (Mochida Pharmaceutical Co., Ltd.) as an anticoagulant was added to the collected blood, and centrifuged at 2,300×g at 4° C. for 10 minutes to collect plasma. The plasma was put in a tube and cryopreserved at −60° C. or lower until measurement.

2.3. Measurement of Bromfenac Concentration in Exudate and Plasma

Methanol was added to the container containing the gauze from which the exudate had been wiped off to extract the exudate. An appropriate amount of acetonitrile was added to the obtained extract, and the mixture was sufficiently stirred and then centrifuged. The supernatant after centrifugation was collected and diluted with a mobile phase A solution described later to prepare a sample solution.

An appropriate amount of acetonitrile was added to the plasma, and the mixture was sufficiently stirred and then centrifuged. The supernatant after centrifugation was collected and diluted with a mobile phase A solution described later to prepare a sample solution. The obtained sample

TABLE 11

|  | Individual | Treatment conditions | |
| --- | --- | --- | --- |
| Example 16 Administration group | a | Extraction socket of right fourth premolar | No collagen sponge preparation is implanted |
|  |  | Extraction socket of left fourth premolar | Collagen sponge formulation of Example 16 is implanted |
|  | b | Extraction socket of right fourth premolar | Collagen sponge formulation of Example 16 is implanted |
|  |  | Extraction socket of left fourth premolar | No collagen sponge preparation is implanted |
|  | c | Extraction socket of right fourth premolar | No collagen sponge preparation is implanted |
|  |  | Extraction socket of left fourth premolar | Collagen sponge formulation of Example 16 is implanted |
| Comparative Example 6 Administration group | d | Extraction socket of right fourth premolar | No collagen sponge preparation is implanted |
|  |  | Extraction socket of left fourth premolar | Collagen sponge formulation of Comparative Example 6 is implanted |
|  | e | Extraction socket of right fourth premolar | Collagen sponge formulation of Comparative Example 6 is implanted |
|  |  | Extraction socket of left fourth premolar | No collagen sponge preparation is implanted |
|  | f | Extraction socket of right fourth premolar | No collagen sponge preparation is implanted |
|  |  | Extraction socket of left fourth premolar | Collagen sponge formulation of Comparative Example 6 is implanted |

2.2. Collection of Exudate and Plasma

At 0.5 hours, 1 hour, 2 hours, 4 hours, 24 hours, 48 hours, 72 hours, 120 hours, and 168 hours after implantation of the collagen sponge formulation, an exudate and blood ware collected.

The exudate was collected by wiping the periphery of the site in which the collagen sponge preparation was embedded with gauze. The weight of the gauze was measured before and after wiping off the exudate, and the amount of the exudate collected was measured. The gauze from which the solution was measured using LC-MS/MS under the following conditions. The average value of each group was calculated from the measured values of the concentration of bromfenac in the exudate and plasma.

LC Conditions

Apparatus: ACQUITY Premier I-Class Systems (Waters)

Column: IM-column InertSustain C18 (2.1 mm I.D.×30 mm, 3 μm, GL Sciences)

Mobile Phase: Ammonium acetate solution (solution A)/methanol (solution B)

Gradient Conditions: The mobile phase A and the mobile phase B were flowed under gradient conditions capable of detecting bromfenac.

Figure 9:
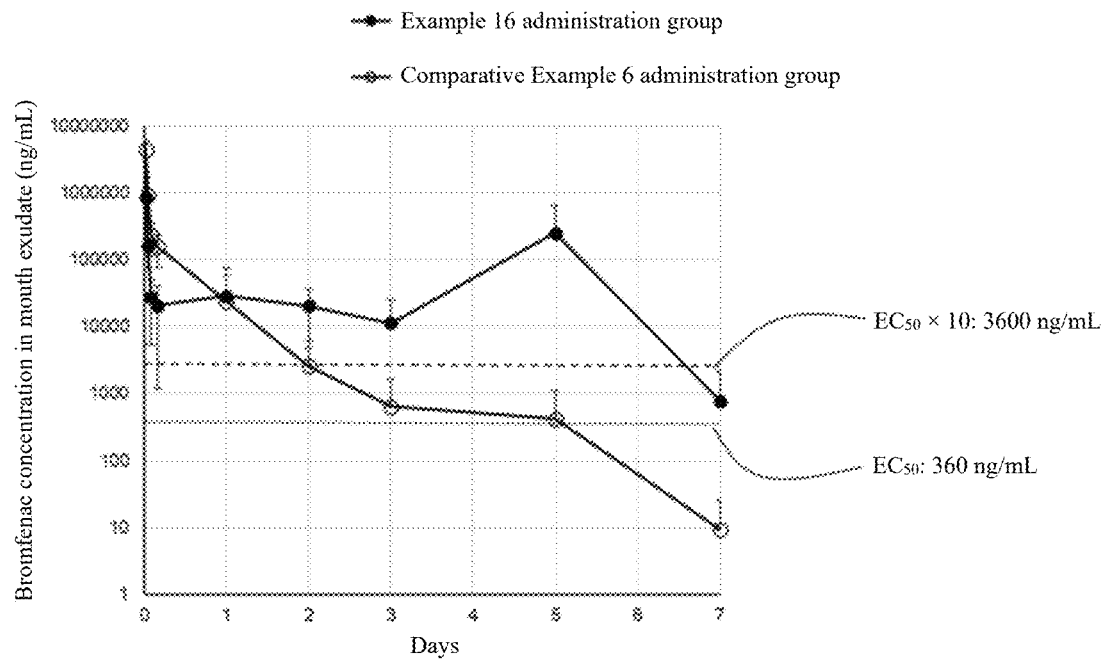
FIG. 9 is a view showing the results of implanting a collagen sponge preparation of Example 16 or Comparative Example 6 in each of the extraction sockets of the left or right fourth premolars of a Beagle dog and chronologically measuring the concentration of bromfenac in an exudate collected from the periphery of a site where the collagen sponge preparation is implanted.

MS/MS Conditions
  Apparatus: Xevo TQ Absolute (Waters)
  Scan type: MRM (Multiple Reaction Monitoring)
  Ionization mode: ESI (Electrospray ionization)
  Polarity: Positive 3. Results The results of the concentration of bromfenac in the exudate are shown in FIG. 9. Since the exudate subjected to the measurement in this test was collected from the periphery of the extraction fossa in which the collagen sponge preparation was embedded, it reflects the bromfenac concentration in the gingival tissue of the extraction fossa. In the Comparative Example 6 administration group, the concentration of bromfenac was 3600 ng/mL or more until 24 hours after implantation of the collagen sponge preparation, but the concentration of bromfenac was less than 360 ng/ml for 168 hours. In contrast, in the Example 16 administration group, the concentration of bromfenac was maintained at 3600 ng/ml or more, which was 10 times or more the concentration of $EC_{50}$, for 120 hours after implantation of the collagen sponge preparation. Furthermore, the concentration of bromfenac was maintained at 360 ng/ml or more, which was $EC_{50}$, for 168 hours. That is, also from the present results, it has been confirmed that a shaped body obtained by drying a raw material aqueous solution to which collagen, an alkali metal salt of bromfenac, and a water-soluble divalent metal salt are added can maintain the concentration of bromfenac at 10 times or more the concentration of $EC_{50}$ for at least 3 hours after application to the tissue defect, and can maintain the concentration of bromfenac at $EC_{50}$ or more for at least 7 days after application.

Figure 10:
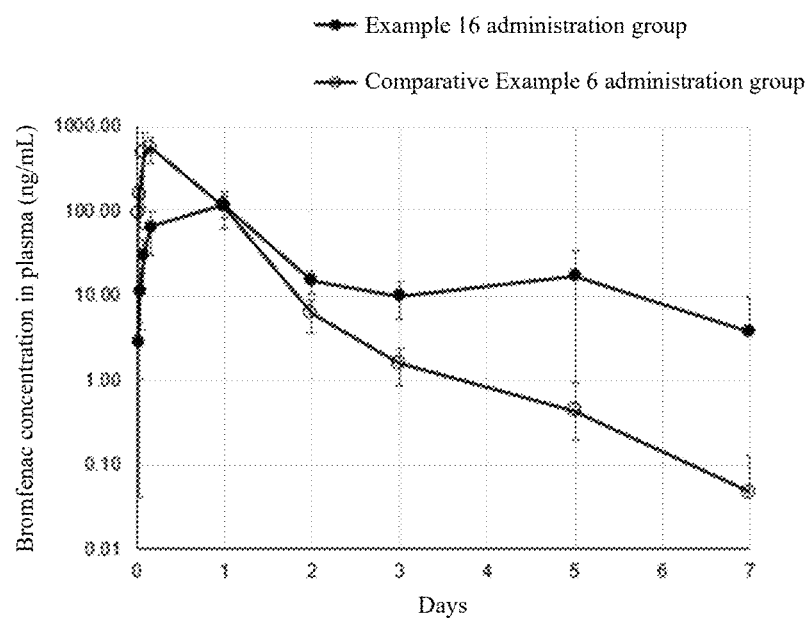
FIG. 10 is a view showing the results of implanting a collagen sponge preparation of Example 16 or Comparative Example 6 in each of the extraction sockets of the left or right fourth premolars of a Beagle dog and chronologically measuring the concentration of bromfenac in plasma.

The results of the concentration of bromfenac in plasma here are shown in FIG. 10. In the Example 16 administration group, the presence of bromfenac in the plasma could be confirmed until 168 hours after implantation of the collagen sponge preparation, and bromfenac was confirmed to be continuously released and absorbed for at least 7 days after implantation of the collagen sponge preparation.

Test Example 7

1. Production of Bullet-Shaped Collagen Sponge Preparation

Collagen (bovine dermis-derived type I atelocollagen, KOKEN CO., LTD. (Japan), manufacturer product number CLP-01) was used to prepare a bullet-shaped collagen sponge preparations (bullet-shaped sponge-like shaped body, diameter of cylindrical portion: about 10 mm, height: about 20 mm) having compositions shown in Table 10 in the same manner as in Test Example 12.

2. Method for Evaluating Stability of Bromfenac in Collagen Sponge Preparation

The obtained collagen sponge preparation was stored in a 2 mL polypropylene container at 80° C. for 3 days or at 60° C. for 2 weeks. After the storage, the collagen sponge preparation was taken out from the polypropylene container, and the mass of the collagen sponge preparation was measured. An appropriate amount of a hydrous acetonitrile solution (volume ratio of acetonitrile:water was 1:1) was then added thereto, followed by heating to extract bromfenac from the collagen sponge preparation. The obtained extraction liquid of bromfenac was diluted so as to have a concentration suitable for measurement, and used as a sample solution. The concentration of bromfenac in the sample solution was measured by high performance liquid chromatography (HPLC), and a related substances of bromfenac generated in the preparation was determined according to the following formula. The related substances of bromfenac refer to those resulting from the degradation of bromfenac.

Mass of each related substance [Expression 2]
  to bromfenac sodium 1.5 hydrate (%) =
  amount of bromfenac sodium 1.5 hydrate converted
  as dehydration product [mg] × $(A_T/A_S)$ × $(1/RF)$ × $(1/4)$ ×
  (383.17/356.16)/dilution magnification correction value $A_T$: Peak area of each related substance of sample solution $A_S$: Peak area of bromfenac in standard solution (concentration of bromfenac in standard solution: 0.005 mg/mL)

RF: Sensitivity coefficient (RF=1.4 in case of related substance in which relative retention time (RRT) to bromfenac appears in about 2.6, RF=1 in the other case)

1/4: Correction value to dilution multiple difference between standard solution and sample solution Dilution magnification correction value: Correction value of dilution magnification of sample solution (0.8 to 4)

Total amount of related substance (%) =
  Sum of amounts of related substances to bromfenac
  sodium 1.5 hydrate (%) × mass of evaluated collagen sponge
  preparation [mg]/total amount of components contained in
  one collagen sponge preparation (described in Table 12) [mg]

3. Results

The obtained results are shown in Table 12. From these results, it became clear that in a shaped body obtained by drying a raw material aqueous solution to which collagen, an alkali metal salt of bromfenac, and a water-soluble divalent metal salt are added, the production amount of the related substance of bromfenac is reduced after storage at 80° C. for 3 days and at 60° C. for 2 weeks as compared with a shaped body obtained under a condition in which a water-soluble divalent metal salt is not added, and therefore the storage stability of bromfenac is improved. In Example 3, the amount of the related substance of bromfenac after the storage at 80° C. for 3 days and at 60° C. for 2 weeks was more than that in Comparative Example 1, but this is presumed to be due to the fact that only the preparation of Example 3 is not stored in an appropriate packaging form, for example, the cap was loose and the sealability was low as compared to others, and factors other than thermal exposure such as moisture absorption are also imparted, and an accurate amount of a related substance could not be observed. From the results of Example 17 and Example 1, it is apparent that when appropriate evaluation is also performed in Example 3. the production amount of the related substance of bromfenac would be reduced as compared with Comparative Example 1.

TABLE 12

| | Examples | | | | | | | Comparative Example |
|---|---|---|---|---|---|---|---|---|
| | 17 | 3 | 1 | 4 | 2 | 5 | 6 | 1 |
| Bromfenac sodium 1.5 hydrate | 8 mg | 8 mg | 8 mg | 8 mg | 8 mg | 8 mg | 8 mg | 8 mg |
| Calcium chloride dihydrate | 0.2 mg | 0.4 mg | 0.8 mg | 1.2 mg | 1.6 mg | 2.0 mg | 2.4 mg | — |
| Collagen | 10 mg | 10 mg | 10 mg | 10 mg | 10 mg | 10 mg | 10 mg | 10 mg |
| Trometamol | 2.5 mg | 2.5 mg | 2.5 mg | 2.5 mg | 2.5 mg | 2.5 mg | 2.5 mg | 2.5 mg |
| Total | 20.7 mg | 20.9 mg | 21.3 mg | 21.7 mg | 22.1 mg | 22.5 mg | 22.9 mg | 20.5 mg |
| Equivalent (Eq) in terms of calcium atom of calcium chloride dihydrate per 1 Eq as equivalent in terms of free form of bromfenac sodium 1.5 hydrate | 0.13 | 0.26 | 0.52 | 0.78 | 1.04 | 1.30 | 1.56 | 0.0 |
| Total amount of related substance (%) After storage at 80° C. for three days | 1.86% | 2.80% | 1.40% | 1.59% | 0.26% | 0.19% | 0.06% | 2.43% |
| After storage at 60° C. for two weeks | 0.68% | 1.00% | 0.68% | 0.62% | 0.17% | 0.09% | 0.20% | 0.85% |

In Table, the total of amounts of components is the amount per collagen sponge preparation.

The invention claimed is:

1. A dental preparation which is a shaped body obtained by drying a raw material aqueous solution comprising collagen and/or gelatin (A), a free form and/or alkali metal salt of bromfenac (B), and a water-soluble divalent metal salt (C),
    wherein the water-soluble divalent metal salt (C) is at least one selected from the group consisting of a water-soluble calcium salt and a water-soluble zinc salt.

2. The dental preparation according to claim 1, wherein in the raw material aqueous solution, the ratio of the water-soluble divalent metal salt (C) to the free form and/or alkali metal salt of bromfenac (B) is from 0.01 Eq to 5 Eq.

3. The dental preparation according to claim 1, wherein a content of bromfenac per 1 g of the shaped body is 1 to 800 mg as an amount of bromfenac in terms of free form.

4. The dental preparation according to claim 1, wherein the collagen and/or gelatin (A) is atelocollagen.

5. The dental preparation according to claim 4, wherein a type of the atelocollagen is type I or type III.

6. The dental preparation according to claim 1, wherein the shaped body is a porous body.

7. The dental preparation according to claim 1, wherein the shaped body has a bullet shape.

8. The dental preparation according to claim 1, wherein the dental preparation is usable as a filling or a coating material for a tissue defect in a dental region.

9. The dental preparation according to claim 8, wherein the tissue defect is an extraction socket.

* * * * *